US006933396B2

(12) United States Patent
Whitten et al.

(10) Patent No.: US 6,933,396 B2
(45) Date of Patent: Aug. 23, 2005

(54) PROCESS TO PREPARE PSOROSPERMIN

(75) Inventors: Jeffrey P. Whitten, Santee, CA (US); Michael Schwaebe, San Diego, CA (US); Terrance Moran, San Diego, CA (US)

(73) Assignee: Cylene Pharmaceuticals, San Diego, CA (US)

( * ) Notice: Subject to any disclaimer, the term of this patent is extended or adjusted under 35 U.S.C. 154(b) by 0 days.

(21) Appl. No.: 10/652,117

(22) Filed: Aug. 28, 2003

(65) Prior Publication Data

US 2004/0102515 A1 May 27, 2004

Related U.S. Application Data

(60) Provisional application No. 60/407,347, filed on Aug. 30, 2002.

(51) Int. Cl.[7] ...................... C07D 311/78; C07D 311/94

(52) U.S. Cl. ....................................... 549/383; 514/453

(58) Field of Search .......................... 549/383; 514/453

(56) References Cited

U.S. PATENT DOCUMENTS 5,741,813 A 4/1998 Lin et al. .................... 514/455

FOREIGN PATENT DOCUMENTS

EP 0 175 376 3/1986

OTHER PUBLICATIONS

International Search Report for PCT/US03/27190, mailed Apr. 20, 2004, 3 pages.
Cassady et al. (1987). *J Org Chem* 52(3):342–347.
Cassady et al. (1987). *Tetrahedron Lett* 28(27):3075–3078.
Still and Gennari. (1983). *Tetrahedron Lett* 41:4405.

*Primary Examiner*—Ba K. Trinh
(74) *Attorney, Agent, or Firm*—Morrison & Foerster LLP

(57) ABSTRACT

Psorospermin and analogs thereof are made using an enantiomerically selective process

24 Claims, 2 Drawing Sheets

| MTS Cytotoxicity Data | | IC50 Values (μm) | | | |
|---|---|---|---|---|---|
| Cell Line | R,R PsOH | R,R PsOMe | R,S PsOMe | S,R PsOMe | S,S PsOMe |
| 8226 |  | 0.072 | 0.345 | 0.221 | 0.494 |
| MIA PaCa-2 | 0.5 | 0.1 | 0.36 | 0.38 | 1.18 |
| HT-29 | 0.4 | 0.178 | 1.21 | 0.319 | 1.79 |
| MDA-MB-468 |  | 0.181 | 1.29 | 0.405 | 1.73 |
| DU 145 | 0.5 | 0.23 | 0.67 | 0.57 | 2.51 |
| H522 |  | 0.28 | 1.35 | 0.77 | 2.77 |
| HeLa |  | 0.39 | 2.5 | 3.2 | 4.45 |

*FIG. 1*

| Primary PK with PsOH | | | |
|---|---|---|---|
| Time (h) | Plasma Concentration (ng/ml) | | |
|  | 1 | 2 | 3 |
| 0.5 | 6.91 | 8.02 | 23.1 |
| 1.0 | BQL | 2.30 | BQL |
| 2.0 | BQL | BQL | BQL |
| 4.0 | 10.5 | BQL | BQL |
| 24.0 | BQL | BQL | BQL |

BQL: Below the quantifiable limit < 2.00 ng/ml

*FIG. 2*

PROCESS TO PREPARE PSOROSPERMIN

RELATED APPLICATIONS

This application is related to U.S. provisional application No. 60/407,347 filed Aug. 30, 2002. The content of this application is incorporated herein by reference in its entirety.

TECHNICAL FIELD

The invention relates to a novel enantiomerically selective process to prepare psorospermin enantiomers and enantiomers of psorospermin analogs. The invention also relates to isolated psorospermin enantiomers and analogs produced by this process. In addition, the invention is directed to the methods of treating proliferative conditions using these compounds.

BACKGROUND ART

Psorospermin is one of the active constituents among cytotoxic xanthones derived from *Psorospermum febrifugum* extracts. This extract has been shown to exhibit cytotoxic and in vivo antitumor activity in the P388 mouse leukemia assay.

Psorospermin has two chiral centers in the molecule, each of which can exist in two possible configurations. This gives rise to four combinations: (R,R), (S,S), (R,S) and (S,R). (R,R) and (S,S) are mirror images of each other and are therefore enantiomers; (R,S) and (S,R) are similarly an enantiomeric pair. The mirror images of (R,R) and (S,S) are not, however, superimposable on (R,S) and (S,R), which are diastereomers. The psorospermin natural product is the 2'R, 3'R enantiomer.

In addition, Cassady 1 (*J. Org. Chem.*, 52:3, 342–347 (1987)) discloses a non-chiral route (±) to 2'R, 3'S 5-methoxy-psorospermin. That is, this reference discloses a process for making a mixture of 2'R, 3'S and 2'S, 3'R without separating these components. Additionally, this reference is directed to making only the 5-methoxy (5-OMe) compound. Because Cassady 1 only discloses the 5-OMe derivative, the process disclosed in that document could be used with a variety of reducing agents, such as LiAlH$_4$ (LAH), for the reduction of the unsaturated ester to the allylic alcohol. As many substituents are susceptible to LAH reduction, it would be useful to develop a process that overcomes this disadvantage. Cassady 1 also discloses a Wittig reaction to make an E (trans) olefin. It would be advantageous to selectively produce cis olefins and ultimately stereoselectively prepare enantiomers of psorospermin as is achieved through the process of the invention.

Cassady 2 (*Tetrahedron Lett.*, 28, 27, 3075–3078 (1987)) disclosed the preparation of a substituted phenol having a Z (cis) olefin and used a Sharpless epoxidation to prepare a chiral epoxide, however, psorospermin or analogs thereof were not synthesized.

It would be useful to develop a process for making psorospermin that would overcome these disadvantages mentioned above as achieved by the method of the present invention.

DISCLOSURE OF THE INVENTION

The present invention allows the selective production of substantially optically pure psorospermin enantiomers and analogs in a cost effective and less time consuming manner, and without other disadvantages of conventional purification methods. Specifically, the process involves an enantiomerically selective process that results in an optically active psorospermin or analog that avoids the use of costly chiral methods to separate the enantiomers and by using a particular combination of reagents or reactants that allows the production of a variety of psorospermin analogs.

Psorospermin (+) 2'R,3'R-(5,10-dimethoxy-2-(2-methyloxiranyl)-1,2-dihydro-3,11 -dioxa-cyclopenta[a]anthracen-6-one) and its closely related analogs are represented by the following formula:

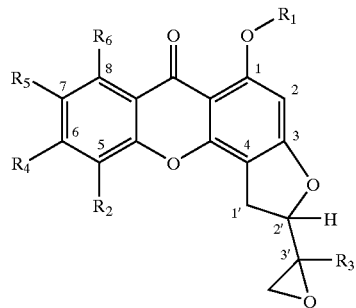

wherein each of R$_1$ and R$_3$ is H or alkyl, preferably methyl;

wherein R$_2$ is H, OH, substituted or unsubstituted alkyl, OR$_2$', wherein the substituted alkyl is 1–6C alkyl substituted with —COOR$_7$, ≡N, or heteroalkyl, wherein R$_7$ is H or alkyl, and wherein R$_2$' is alkyl or a protecting group preferably benzyl;

wherein each of R$_4$, R$_5$, and R$_6$ is H, alkyl, or 2–10C alkoxy; wherein two adjacent residues of R$_2$, R$_4$, R$_5$, and R$_6$ can form a fused cyclic, aromatic or heterocyclic ring having 5–7 members.

The stereochemistry at the 2' and 3' positions for psorospermin and analogs thereof are as follows:

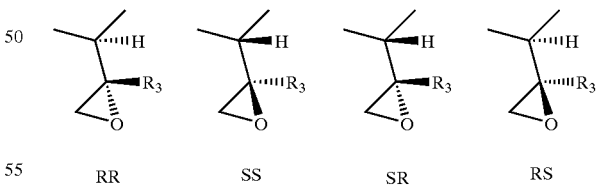

The inventive methods of making these substantially optically pure compounds rely on particular reactants used in various steps of the reaction schemes. In two different steps subsequent to the preparation of the xanthone backbone, the substituents on the 4 position of the xanthone are manipulated such that the resulting psorospermin or analog thereof contains the appropriate predetermined stereochemistry.

In one embodiment, a process for preparing a substantially optically pure psorospermin or analog of the formula:

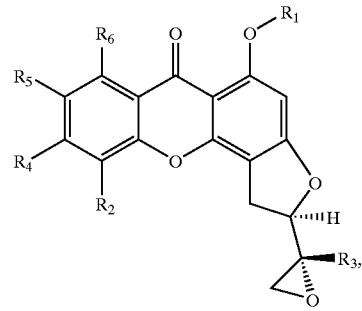

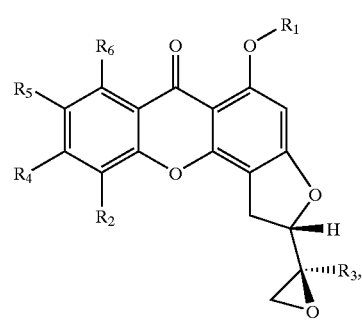

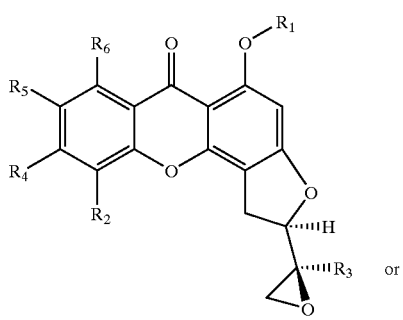 or

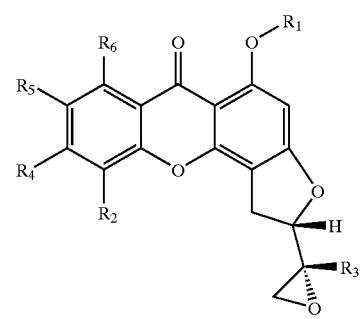

wherein each of $R_1$ and $R_3$ is H or alkyl;

wherein $R_2$ is H, OH, substituted or unsubstituted alkyl, $OR_2'$, wherein the substituted alkyl is 1–6C alkyl substituted with —$COOR_7$, ≡N, or heteroalkyl, wherein $R_7$ is H or alkyl, and wherein $R_2'$ is alkyl or a protecting group;

wherein each of $R_4$, $R_5$, and $R_6$ is H, alkyl, or 2–10C alkoxy; wherein two adjacent residues of $R_2$, $R_4$, $R_5$, and $R_6$ can form a fused cyclic, aromatic, heteroaromatic or heterocyclic ring having 5–7 members, the process comprising:
deprotecting a compound of the formula:

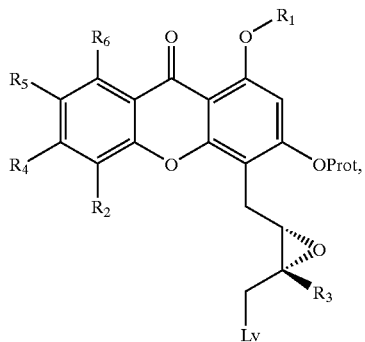

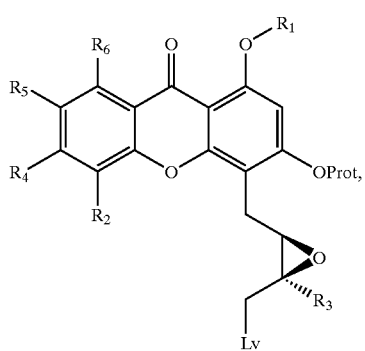

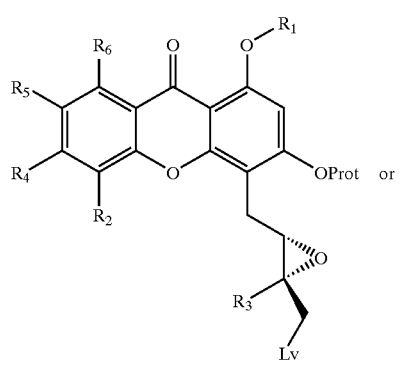 or

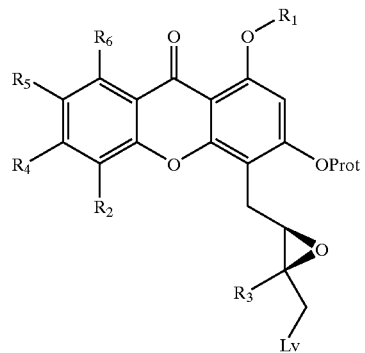

wherein $R_1$ and $R_3$–$R_6$ are defined above, $R_2$ is H, alkyl, O-alkyl or an O-protecting group, Prot is a protecting group, and Lv is a leaving group.

In a preferred embodiment, the deprotecting conditions in the deprotecting step comprise Pd/BaSO$_4$ and 1,4-cyclohexadiene or Raney Nickel.

In another embodiment of the process above, wherein $R_2$ is OH after the deprotecting step, further comprises alkylating

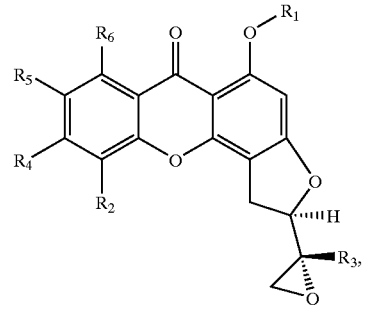

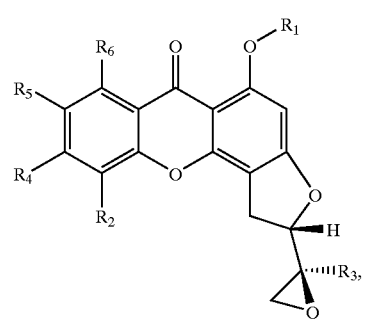

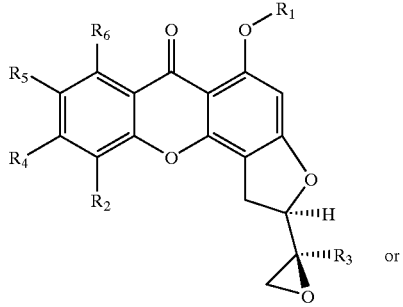

or

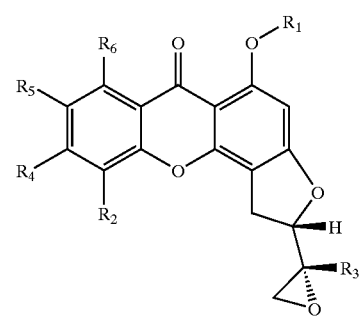

wherein $R_2$ is $OR_2'$ where $R_2'$ is alkyl after the alkylating step.

In a further embodiment, the process above comprising before the hydrogenating step, chirally epoxidizing

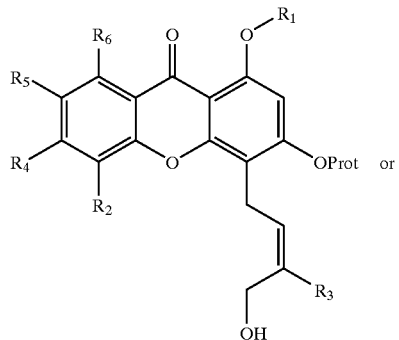

or

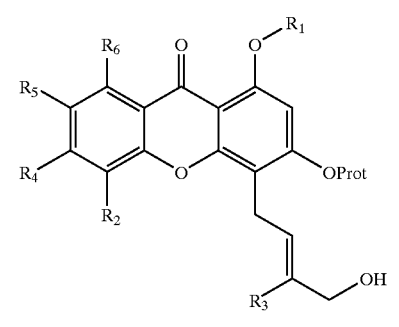

wherein $R_1$ and $R_3$–$R_6$ are defined as above and $R_2$ is H, alkyl or a protected hydroxyl group to form

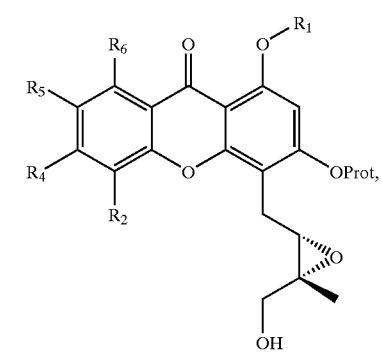

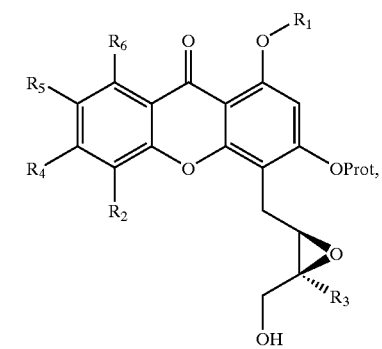

-continued

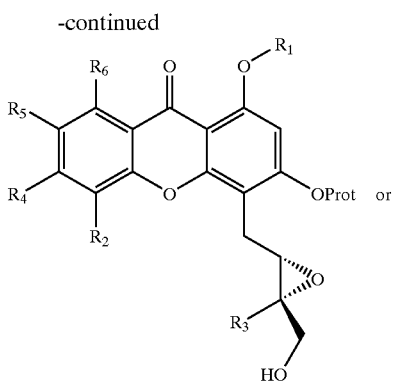

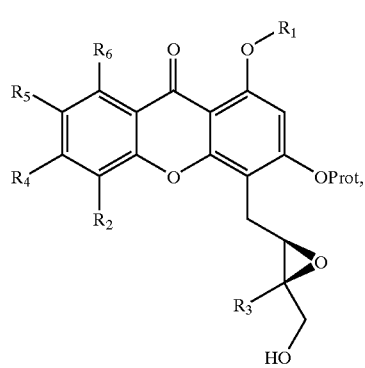

and modifying the hydroxyl at the 4' position into a leaving group.

In a preferred embodiment, either of

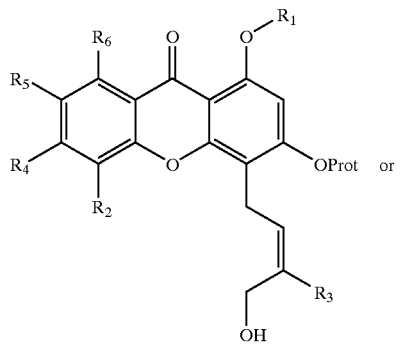

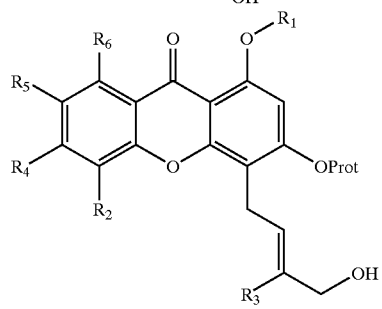

is epoxidized with of either (−) DIPT or (+) DIPT and the leaving group is provided by mesylation of the hydroxyl group.

In yet another embodiment, the above process further comprises before the chiral epoxidizing step, forming an unsaturated ester under either cis- or trans-directing reaction conditions

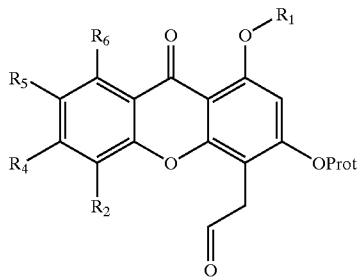

wherein $R_1$ and $R_4$–$R_6$ are defined above, $R_2$ is H, alkyl or a protecting group, and Prot is a protecting group, to form a cis or trans ester of the formula

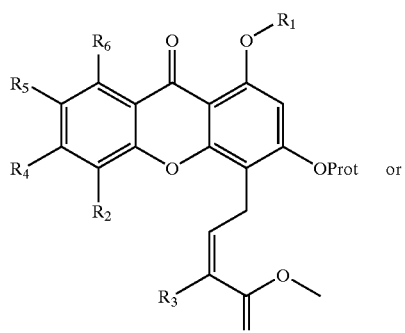

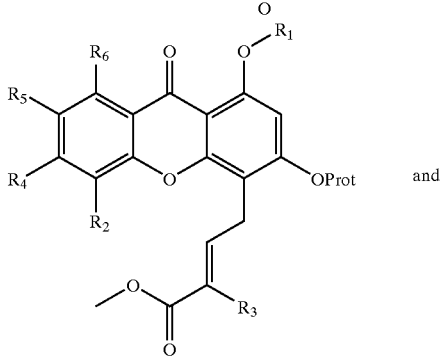

subsequently reducing the ester to an allylic alcohol of the formula

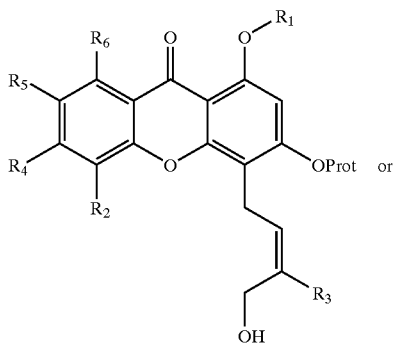

-continued

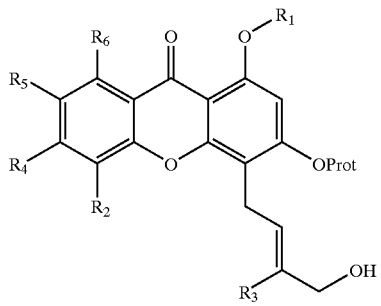

wherein $R_1$ and $R_3$–$R_6$ are defined above, $R_2$ is H, alkyl or a protecting group, and Prot is a protecting group.

In a preferred embodiment, the cis-directing reaction conditions are $(CF_3CH_2O)_2POCH(R_3)CO_2Me$ or $(PhO)_2POCH(R_3)CO_2R$, where R is an alkyl group and Ph can be substituted, in KHMDS/18-crown-6 and the trans-directing reaction conditions are $(CH_3CH_2O)_2POCH(R_3)CO_2R$ wherein R is alkyl; and wherein the ester is reduced with DIBALH.

In another embodiment the process further comprises before the esterifying step, selectively protecting the hydroxyl group at the 3 position and a hydroxyl group at the 5 position, if $R_2$ is OH as in the following compound:

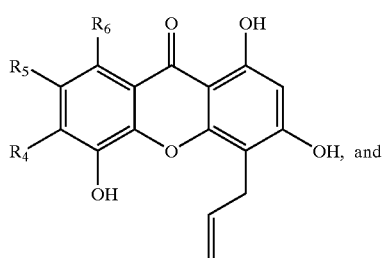

wherein $R_1$ and $R_4$–$R_6$ are defined above, to form

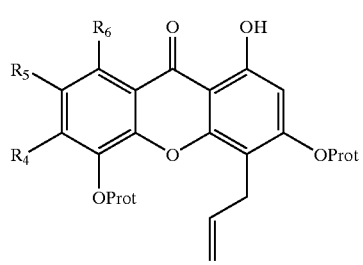

wherein $R_2$ is $OR_2'$ and $R_2'$ is a protecting group, OProt is a protected hydroxyl group and $R_1$ and $R_4$–$R_6$ are defined above, alkylating the hydroxyl group at the 1 position, and forming an aldehyde at the 3' position to form

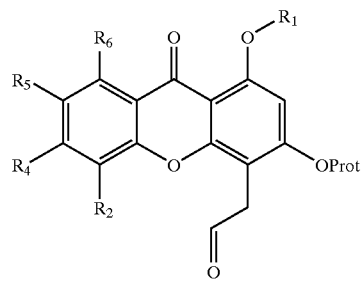

wherein $R_2$ is $OR_2'$ and $R_2'$ is a protecting group.

In a preferred embodiment, the protecting group on the hydroxyl group at the 3 and 5 positions is a benzyl group.

In another embodiment the process further comprises before the protecting step, dealkylating

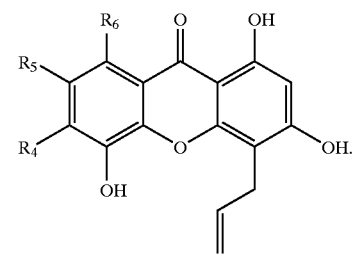

wherein $R_1$ is alkyl and $R_2$ is $OR_2'$ and $R_2'$ is alkyl, and wherein $R_4$–$R_6$ are as defined a to form

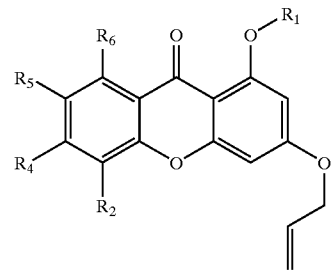

In a preferred embodiment, $R_1$ and $R_2$ are each methyl before the dealkylating step and $BBr_3$ is used as a demethylation agent in the dealkylating step.

In another embodiment the process above further comprises before the dealkylating step rearranging wherein $R_1$ is alkyl and $R_2$ is $OR_2'$ and $R_2'$ is alkyl to form

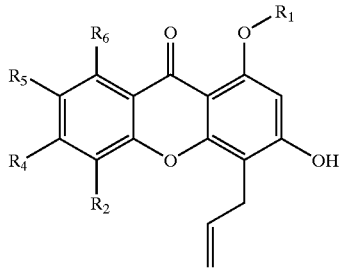

wherein $R_1$ is alkyl and $R_2$ is $OR_2'$ and $R_2'$ is alkyl under Claisen conditions such that cyclization does not result. In a preferred embodiment, the Claisen conditions comprise heating about 190° C.

In the processes above it is preferred that R,R psorospermin, R,S psorospermin, S,R psorospermin, S,S psorospermin, R,R 5-methoxypsorospermin, R,S 5-methoxypsorospermin, S,R 5-methoxypsorospermin, or S,S 5-methoxypsorospermin is produced.

Thus, in one aspect, the invention is directed to methods to produce these compounds. In other aspects, the invention is directed to compounds made by these processes, to pharmaceutical compositions containing them, and to methods of treating proliferative disorders using these compounds.

In addition, it has been found that the 2'R,3'R 5-methoxypsorospermin in particular has surprisingly advantageous properties. In particular, this 5-methoxy-psorospermin has been shown to have prolonged systemic presence in comparison with 2'R,3'R psorospermin.

BRIEF DESCRIPTION OF THE DRAWINGS

FIG. 1 illustrates a comparison of (R,R)-psorospermin with (R,R)-5-methoxy-psorospermin, (R,S)-5-methoxy-psorospermin, (S,R)-5-methoxy-psorospermin and (S,S)-5-methoxy-psorospermin in cell viability assays with various tumor cell lines.

FIG. 2 shows the primary PK in (2'R,3'R) psorospermin.

MODES OF CARRYING OUT THE INVENTION

Figure 3:
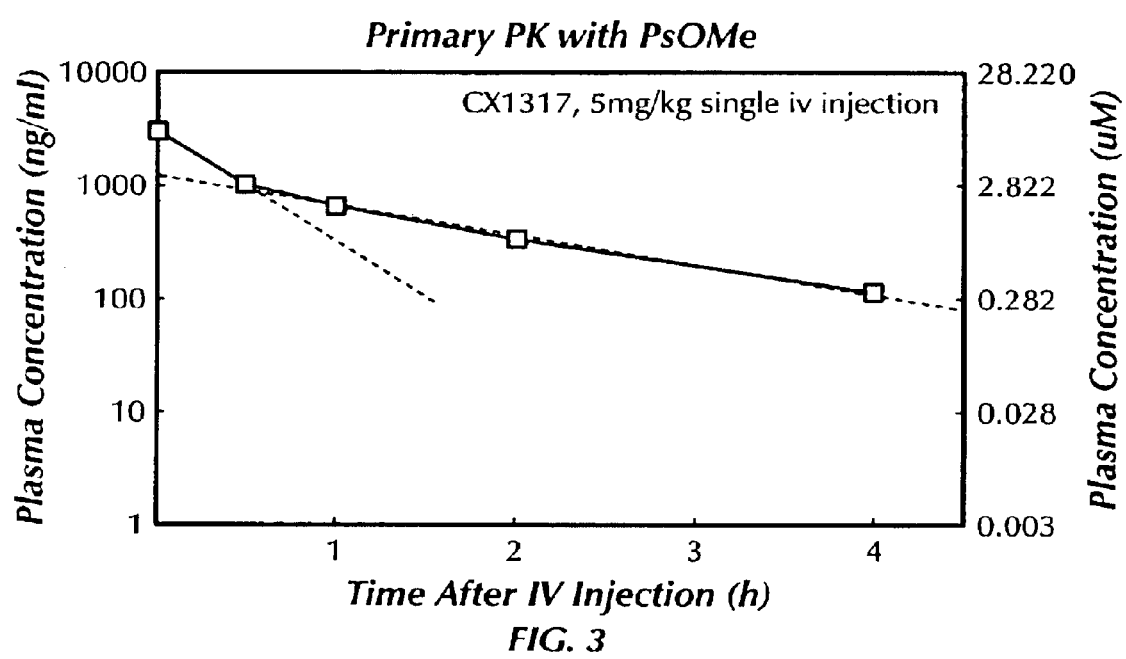
FIG. 3 shows the primary PK in (2'R,3'R) 5-methoxy-psorospermin.

The methods of the invention provide for the selective production of substantially optically pure enantiomers of psorospermin. Such selective production of various enantiomers of psorospermin or its analogs allows substantially optically pure enantiomers to be prepared without the need to separate the enantiomers using expensive chiral separation methods.

In one aspect of the invention, psorospermin or analog thereof is made from the starting materials of substituted benzoic acid and phloroglucinol or derivative of either. The R groups are as defined above unless otherwise indicated. In step 1 of this method, a xanthone is prepared by the condensation of a substituted benzoic acid and phloroglucinol or derivative thereof as represented by the following illustrative reaction:

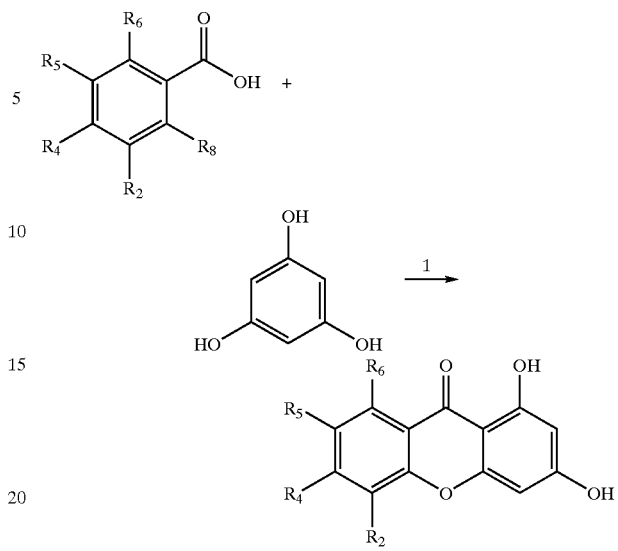

$R_8$ is any appropriate functional group for condensation such as halo, alkoxy, hydroxy or diazo, and preferably alkoxy. Preferably $R_2$ is alkoxy, more preferably methoxy (as shown in Reaction Schemes 1–2, 4, 6–7 and 9), or is H (as shown in Reaction Schemes 3, 5, 8 and 10). Derivatives of phloroglucinol include those in which one, two, or three of the hydroxyls are replaced by an alkoxy or sulfonate moiety. A Lewis acid or substance that acts as a Lewis acid can be used as the condensation reagent. Preferably a Lewis acid in a solvent is used such as $ZnCl/POCl_3$ is used or a Lewis acid such as $H_2SO_4$ is used. Most preferably $ZnCl/POCl_3$ is used. Other materials that act as a Lewis acid such as $MsOH/P_2O_5$ may also be used.

Once the tricyclic xanthone is formed, the substituents in the 1, 3 and 5 positions can be manipulated based on groups desired in the resulting psorospermin or analog in steps 2 and 3. First, with respect to the 1 and 3 positions, assuming, in one aspect, underivatized phloroglucinol is used in step 1, the hydroxyl group at the 3 position is allylated and the hydroxyl group at the 1 position is alkylated as illustrated by the following reaction scheme:

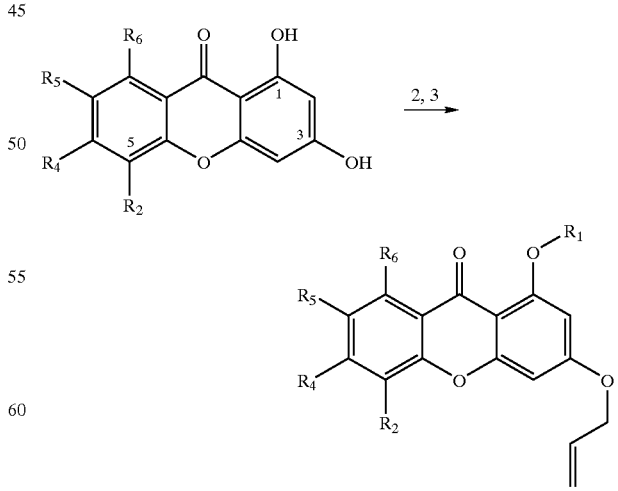

wherein $R_1$ is alkyl.

Any allylating agents may be used to allylate the 3 position hydroxyl such as an allyl halide with a mild base.

Preferably, the reagents used are allyl halides such as allyl bromide, allyl iodide, or allyl chloride with mild bases such as $K_2CO_3$, $NaHCO_3$, or $Et_3N$. In another embodiment, allyl alcohol/$PPh_3$/DEAD is used. In a more preferred embodiment, allyl bromide/$K_2CO_3$ is used. In addition, any alkylating agent can be used to alkylate the hydroxyl group at the 1 position, for example, any alkyl halide such as $R_1I$(wherein $R_1$ is alkyl), dimethyl sulfate, preferably in the presence of a mild base such as $K_2CO_3$, NaH, and any solvent such as DMF or acetone. Alternatively, Mitsunobu conditions such as methanol/$PPh_3$/DEAD are used. Most preferably $R_1I/K_2CO_3$ or $CH_3I/K_2CO_3$.

Next, an ortho-Claisen rearrangement provides an allyl group at the 4 position, while leaving a hydroxyl group at the 3 position as illustrated below in step 4:

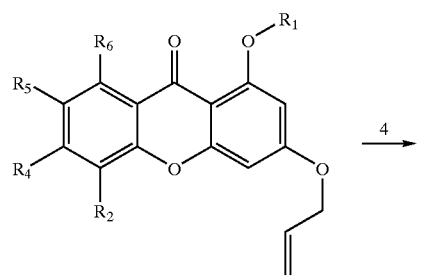

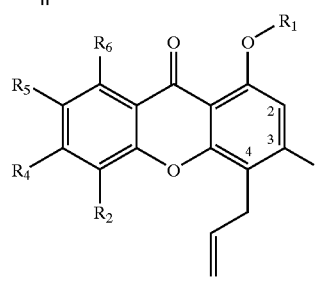

Any Claisen reaction conditions can be used where cyclization does not result or the xanthone's 2 position is not substituted with the allyl group instead of the 4 position. Preferably, heat is used as the primary reaction condition, preferably at a temperature of from about 180°–200° C., and preferably about 190° C. In addition, solvents may be used such as mesitylene, xylene, toluene, diphenyl ether, N,N-dimethyl aniline, or N,N-diethyl aniline. Preferably heat alone or heat with mesitylene solvent are preferred.

In the next step, step 5, the xanthone's 1 and 5 positions are dealkylated, if $R_2$ is alkoxy as shown by the illustrative reaction below:

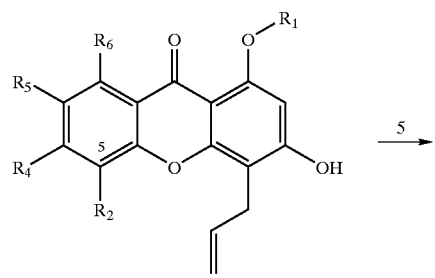

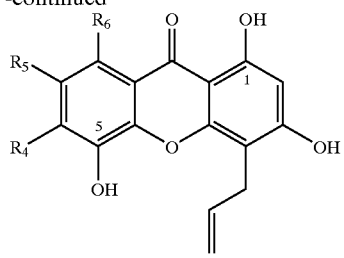

Any dealkylating agent may be used that allows further manipulation of the 1 and 5 positions. Preferably, Lewis acids are used, and more preferably $BBr_3$, TMSI, $BCl_3$, or LiCl/DMF and most preferably $BBr_3$. Of course, if $R_2$ is H (as shown in Reaction Schemes 3, 5, 8 and 10) or $OR_2'$ where $R_2'$ is the preferred substituent in the resulting psorospermin analog, for example, if $R_2$ in the benzoic acid starting material was H or $OR_2'$, or the starting material was the compound in step 4 where $R_2$ was H or $OR_2'$, it would not be necessary to perform this step.

In the following step 6, the xanthone's 3 and 5 positions are protected as shown in the following illustrative reaction:

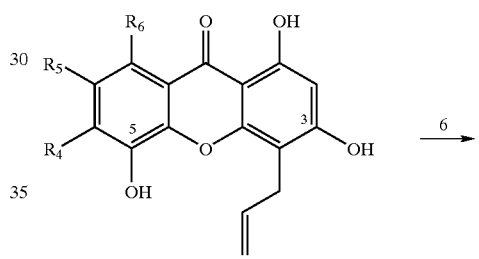

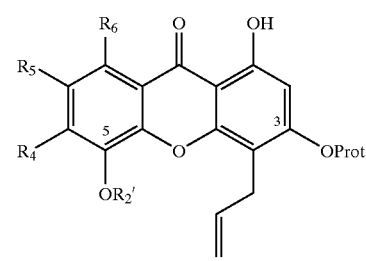

wherein $R_2'$ is a protecting group and OProt at position 3 is a protected hydroxyl group. Any reagents that will provide a protecting group at these positions, which protecting groups can withstand reductive conditions, can be used, such as BnBr, benzyl alcohol/$P(Ph)_3$/DEAD, benzyl chloride as well as any weak base, such as $NaHCO_3$, $K_2CO_3$, or $Et_3N$ and any solvent such as DMF and preferably the combination BnBr/$K_2CO_3$/DMF. Of course, if a compound was provided previously to step 4 wherein $R_2$ was an alkoxy group or another group that acted as a protecting group, the previous dealkylation step 5, and this protection step 6 would be unnecessary with respect to the 5 position. Further, if $R_2$ is H, the dealkylation and protection steps also would be unnecessary as illustrated in Reaction Schemes 3, 5, 8 and 10. This protection step is necessary for the protection of the 3 position hydroxyl, however, because an unprotected hydroxyl group results from the Claisen rearrangement.

If it is desirable to alkylate a hydroxyl group at the 1 position, step 7 below illustrates such a reaction:

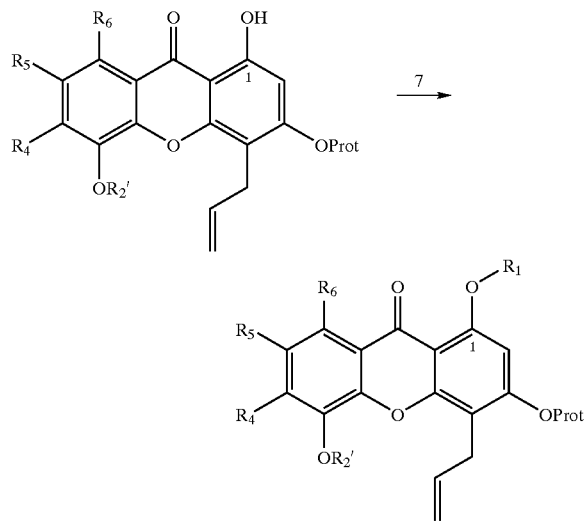

wherein $R_2'$ is a protecting group and OProt at position 3 is a protected hydroxyl group.

Any alkylating agent such as an alkyl halide can be used. Preferably, an alkyl halide with weak base (e.g., $K_2CO_3$ or NaH) and aprotic solvent or alcohol under Mitsunobu conditions (ROH/P(Ph)$_3$/DEAD) or similar reagent is used, or most preferably $R_1I$ with DMF (as shown in Reaction Schemes 4, 6–7, and 9), and more preferably $CH_3I$ with DMF (as shown in Reaction Schemes 1–2). Reaction Schemes 3, 5, 8 and 10 illustrate another embodiment of the invention where $R_1$ is alkyl (i.e., there is an alkoxy group at position 1).

Step 8 below, illustrates the oxidative cleavage of the allyl group on the 4 position to an aldehyde.

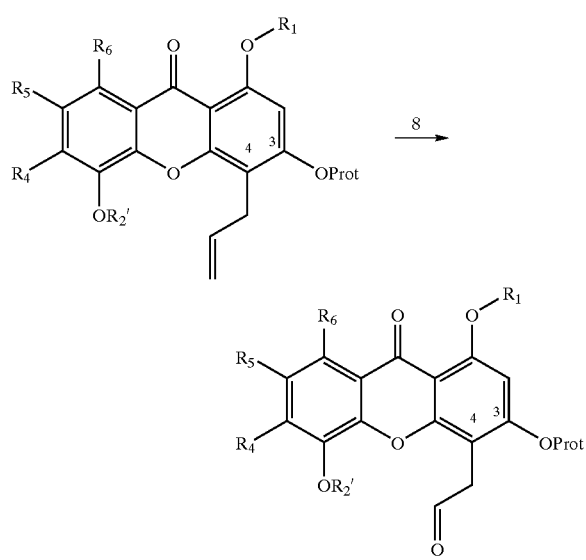

wherein $R_2'$ is a protecting group and OProt at position 3 is a protected hydroxyl group.

Any oxidizing agent can be used that results in an aldehyde. Preferably $OsO_4/NaIO_4$, ozone, or ruthenium catalysts with $NaIO_4$, and preferably $OsO_4/NaIO_4$ is used.

The aldehyde group in the following step 9 is converted to the ester. Different conditions control the particular stereochemistry of the 3' position of psorospermin or its analogs. Depending on such conditions, the unsaturated ester at the 4 position of the xanthone that is formed in step 9 will have either a cis or trans configuration. In particular, if it is desirable that the resulting stereochemistry of psorospermin or its analogs is the same at both the 2' and 3' position (i.e., 2'R,3'R or 2'S,3'S), the ester group must be in the cis position relative to the xanthone backbone on the same side of the olefin's double bond. In contrast, if it is desirable that the resulting stereochemistry of psorospermin or its analog differ at the 2' and 3' positions (i.e., 2'R,3'S or 2'S,3'R), the ester group must be in the trans position relative to the xanthone backbone on the opposite side of the olefin's double bond.

Step 9 below illustrates a modified Horner/Emmons reaction that results in a cis configuration.

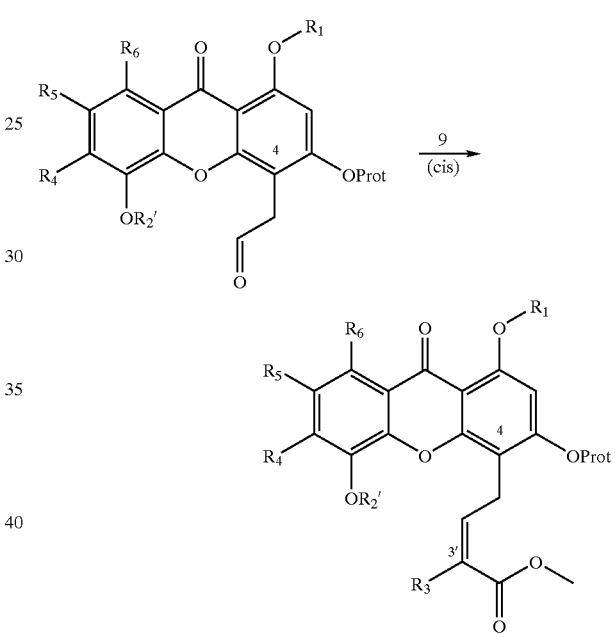

wherein $R_2'$ is a protecting group and OProt at position 3 is a protected hydroxyl group.

For this reaction any Horner/Emmons, modified Horner/Emmons, or Wittig reagent may be used that results in the desired cis or trans configuration. Preferred reagents for a cis-directing reaction is a modified Horner/Emmons reactant such as 18-crown-6, $(CF_3CH_2O)_2POCH(R_3)CO_2Me$ or $(PhO)_2POCH(R_3)CO_2R$, in a base where R is an alkyl group and Ph can be substituted such as with alkyl. In an embodiment, the base is KHMDS, Triton B, K-OTMS, or KH. Preferably the reagent is $(CF_3CH_2O)_2POCH(R_3)CO_2Me$/KHMDS/18-crown-6. Such reactions resulting in a cis configuration are illustrated in Reaction Schemes 1–6.

Preferred reagents for a trans-directing reaction is a Horner/Emmons reactant such as $(CH_3CH_2O)_2POCH(R_3)CO_2Me$ in a similar base, such as NaH. Preferably the reagent is $(CH_3CH_2O)_2POCH(R_3)CO_2Me$. The base is not as sensitive for trans-directing as cis-directing conditions. Reaction Schemes 7–10 illustrate reactions resulting in the trans configuration.

In the next step, step 10, the ester is reduced to an alcohol as illustrated below (the cis configuration is exemplified):

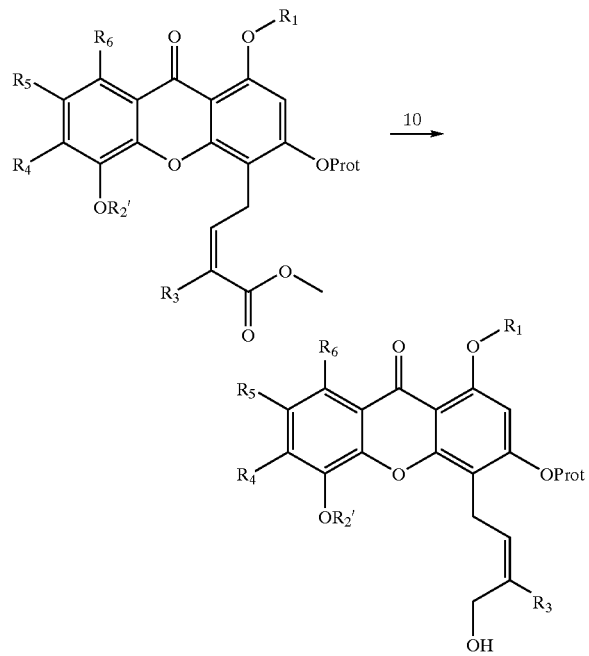

wherein $R_2'$ is a protecting group and OProt at position 3 is a protected hydroxyl group. Any reducing agent can be used that gives selective 1,2 reduction of the ester to give the alcohol and that does not disturb or isomerize the double bond of the olefin group. Preferably DIBALH (diisobutyl aluminum hydride) is used for either cis or trans unsaturated esters. Strong reducing conditions such as LAH can reduce protecting groups on the 3 and 5 hydroxyl moieties (i.e., $R_2'$ and/or Prot) and therefore are not preferred and often are not utilized. Thus, in certain embodiments, LAH is not used as described in Cassady 1 cited above. With respect to the cis ester configuration, it is preferred that reducing agents are avoided that promote the isomerization of the cis configuration to the trans configuration. In one preferred embodiment to make the trans allylic alcohol, hydrolysis (e.g., KOH/EtOH) is followed by methylchloroformate to form a mixed anhydride, which resulting compound is then reduced with a reducing agent such as $NaBH_4$.

Next, the asymmetric (i.e. chiral) epoxidation of the allyl group is illustrated in step 11 below, which illustrates reaction conditions that provide an intermediate that will result in R stereochemistry at the 2' position of psorospermin or its analogs:

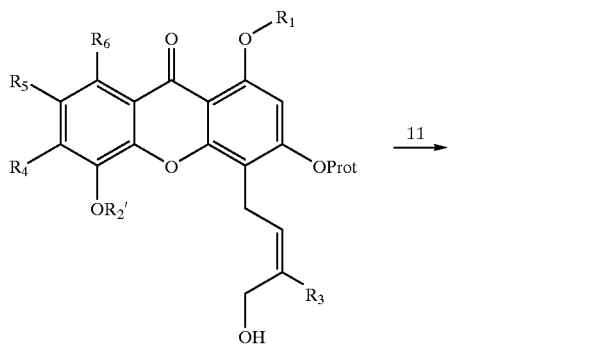

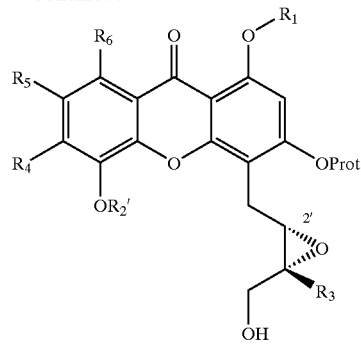

wherein $R_2'$ is a protecting group and OProt at position 3 is a protected hydroxyl group.

Any selective enantiomeric epoxidation conditions can be used, such as Sharpless conditions. Any epoxidation conditions that do not selectively provide an enantiomeric product are not preferred such as meta-chloroperbenzoic acid (MCPBA), which provides the racemate. In one preferred embodiment to arrive at the R stereochemistry at the 2' position of psorospermin or its analogs, (−) DIPT is used as a reactant to form an epoxide precursor as illustrated in Reaction Schemes 1–4 and 7–8 below. Similarly, in another preferred embodiment to arrive at the S stereochemistry at the 2' position, (+) DIPT is used as a reactant to form an epoxide precursor as illustrated in Reaction Schemes 5–6 and 9–10. DIPT is diisopropyl tartrate.

After epoxidation, a leaving group is provided on the 4' hydroxyl of the psorospermin analog, as shown in the reaction below in step 12:

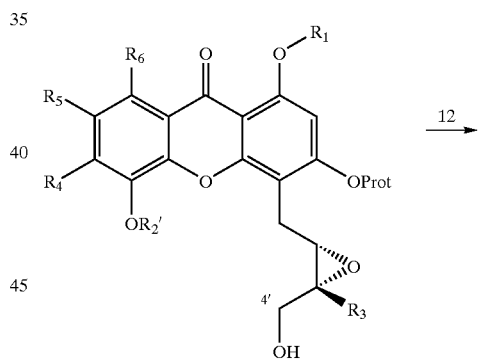

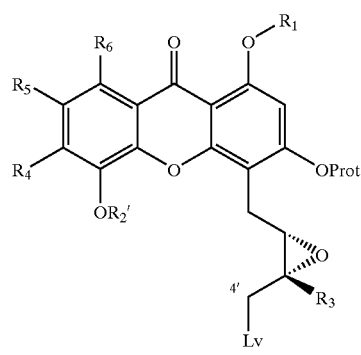

wherein $R_2'$ is a protecting group, OProt at position 3 is a protected hydroxyl group, and Lv is a leaving group.

Any leaving group that does not hydrolyze under the subsequent cyclization conditions can be used. Preferably, providing a leaving group by reagents such as MsCl (methane sulfonyl chloride), TsCl (tosyl chloride), or TfOTf (Triflic anhydride) can be used, preferably in the presence of a weak base such as $Et_3N$, or reagents used to halogenate the 4' position. Mesylation (methyl sulfonylation) of the hydroxyl group is preferred, most preferably using MsCl and $Et_3N$.

In the final steps 13 and 14 the psorospermin or analog are obtained. Step 13 provides deprotection of the protected hydroxyl group at the 3 and 5 positions and cyclization, and step 14 provides alkylation of $OR_2'$ as shown below which illustrates a resulting 2'R,3'R psorospermin or analog configuration:

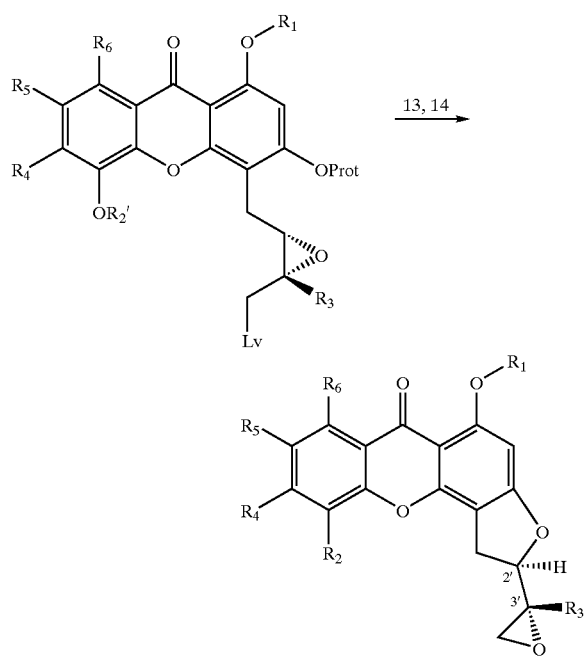

wherein $R_2'$ is a protecting group, OProt at position 3 is a protected hydroxyl group, and Lv is a leaving group.

Of course, if $R_2$ is H or alkyl which is present before this cyclization step, the alkylation step 14 would not be necessary as illustrated in Reaction Schemes 3, 5, 8 and 10. In addition, if OH is desired at $R_2$ of the resulting psorospermin or analog, alkylation would be unnecessary as the $OR_2'$ would result in OH after the hydrogenation step 13. Reaction Scheme 2 illustrates this point.

It is contemplated that any of the intermediates can be used as starting materials in an attenuated process.

The deprotection/cyclization of the epoxide step 13 is obtained by hydrogenation conditions. Any mild hydrogenation conditions can be used. Catalysts such as modified Pd/C or $Pd/BaSO_4$ can be used. Hydrogen or hydrogen equivalents can be used such as $H_2$, or formic acid, or 1,4-cyclohexadiene. In an embodiment, $Pd/BaSO_4$ and 1,4-cyclohexadiene is used, where 1,4-cyclohexadiene is the hydrogen source and $Pd/BaSO_4$ is the catalyst that deprotects or reduces the protected hydroxyl groups (OProt) to hydroxyl and then a base treatment cyclizes to form the furan ring and terminal epoxide. Raney Nickel is used in preferred embodiment, where it sometimes is used catalytically with a hydrogen source (e.g., $H_2$) and sometimes is used stoichiometrically. Base treatments include $K_2CO_3$ in methanol, KOtBu in t-butanol, and more preferably $K_2CO_3$ in methanol, or other mild base treatments that are known in the art. The deprotecting and cyclizing steps can be performed sequentially or at the same time, preferably at the same time. In addition, a solvent may be present in the deprotecting/cyclizing step such as methanol, ethylacetate or ethanol, or mixtures thereof.

Any alkylating agent can be used for alkylation step 14, such as an alkyl halide (e.g., $R_2'I$ or $CH_3I$) and a weak base or alcohol under Mitsunobu conditions, or acid chlorides or alkylsulfonyl chlorides. Most preferably $R_2'I$ or $CH_3I$ is used.

As used herein, the term "alkyl" includes straight- and branched-chain and cyclic monovalent substituents. Examples include methyl, ethyl, isobutyl, cyclohexyl, cyclopentylethyl, and the like. Typically, the alkyl substituents contain 1–10C. Preferably they contain 1–6C. Heteroalkyl is similarly defined but may contain 1–2 O, S or N heteroatoms or combinations thereof within the backbone residue.

"Aromatic" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5–12 ring member atoms.

As used herein, a "protecting group" for a hydroxy includes any suitable group that protects a hydroxyl group from the reactions in the process of the invention such as alkylation, oxidation, esterification, reduction, epoxidation and the addition of a leaving group. Examples of protecting groups are benzyl groups, acyl groups, carbonate groups, and the like. Suitable protecting groups are described by Greene, T. W., et al., in *Protecting Groups in Organic Synthesis*, 2nd Ed., John Wiley & Sons, Inc. (1991), incorporated herein by reference.

"Substantially optically pure" is defined as psorospermin that contains mostly one enantiomer of psorospermin. The processes of the invention are selective in producing one enantiomer over an other enantiomer. More specifically, a substantially optically pure psorospermin contains about 20% or less by weight of a different psorospermin enantiomer, preferably about 0–20%, more preferably about 0–10%, even more preferably about 0–5% or about 0–2% of a psorospermin enantiomer. Most preferably, the substantially optically pure psorospermin contains less than about 1% by weight of other psorospermin enantiomers.

The relationships between the reactants and the final psorospermin compounds and their analogs may be seen more clearly in the following reaction schemes.

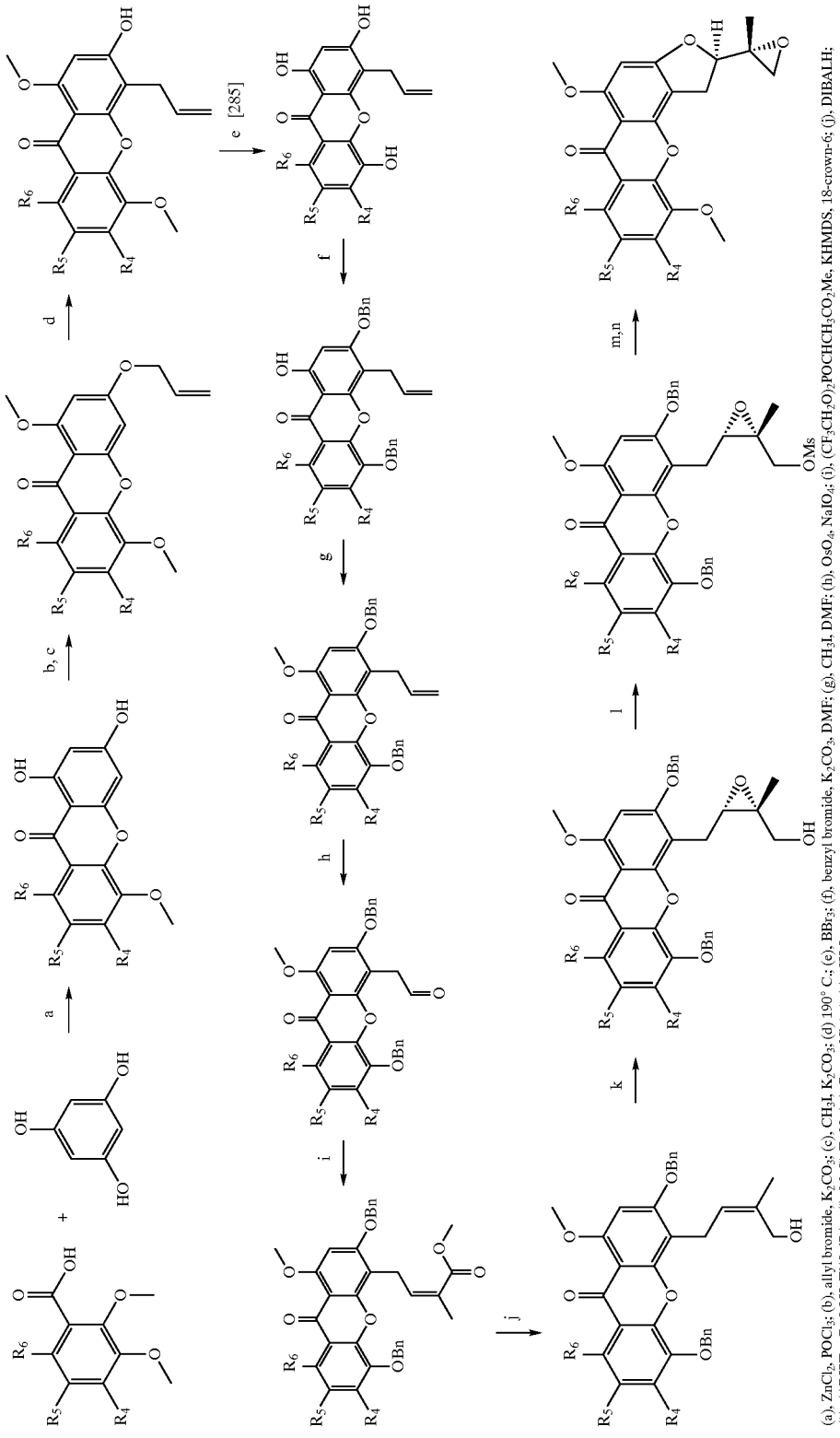

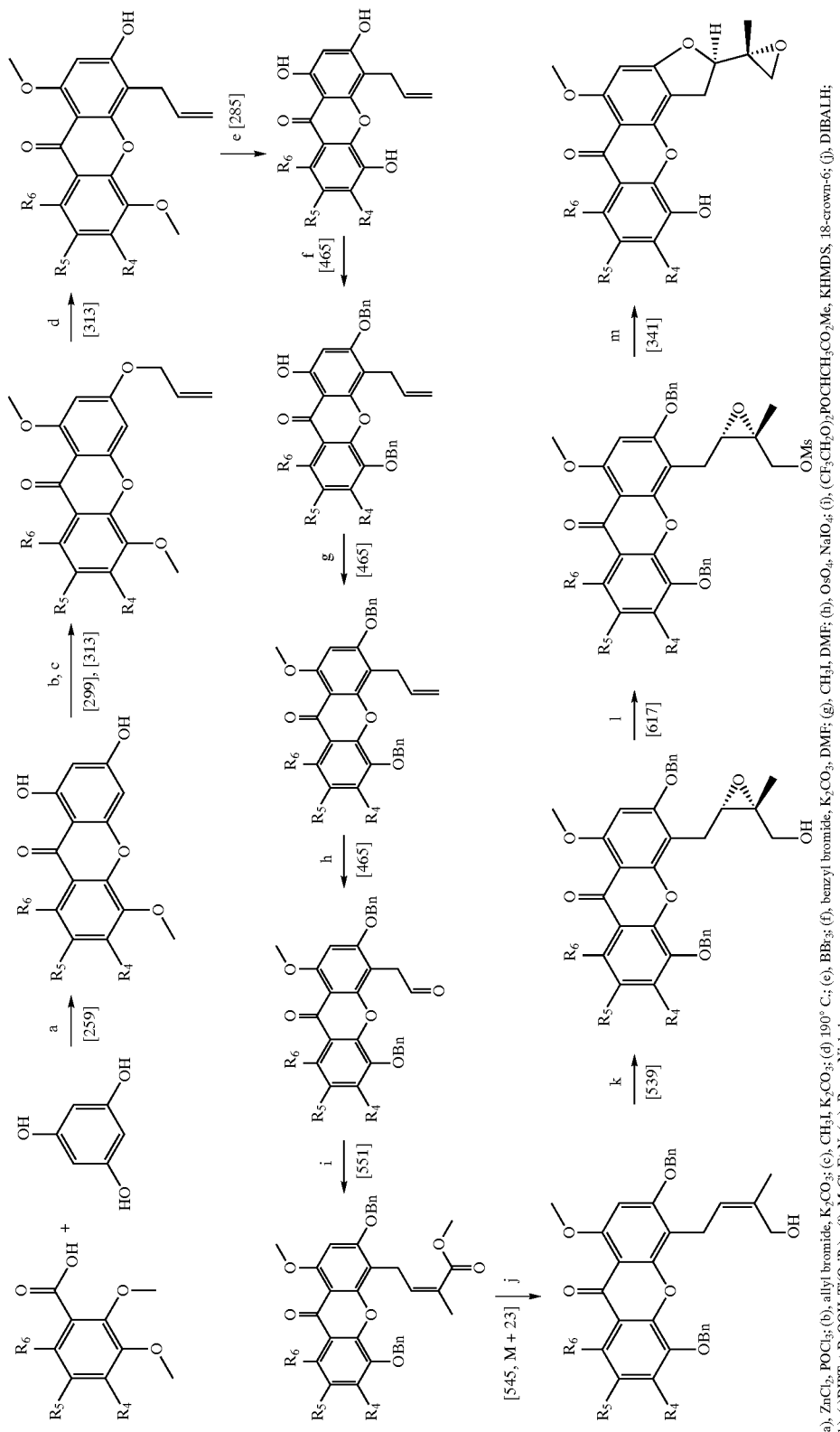

Reaction Scheme 3:
2′R,3′R Psorospermin and Closely Related Analogs (R2 = H)
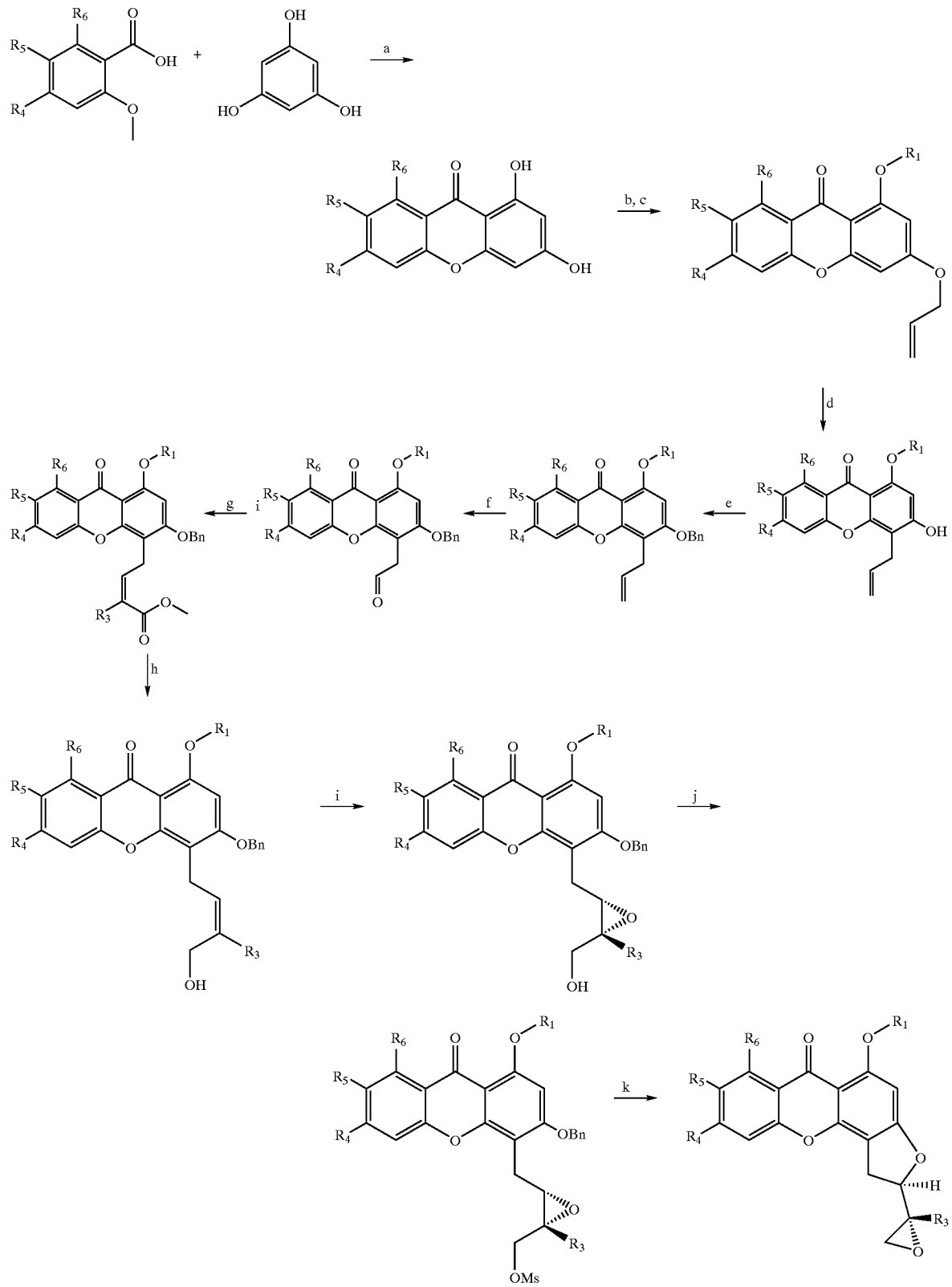
(a), ZnCl₂, POCl₃; (b), allyl bromide, K₂CO₃; (c), R₁I, K₂CO₃; (d) 190° C.; (e), benzyl bromide, K₂CO₃, DMF; (f), OsO₄, NaIO₄;
(g), (CF₃CH₂O)₂POCHR₃CO₂Me, KHMDS, 18-crown-6; (h), DIBALH; (i), (-)DIPT, t-BuOOH, Ti(O-iPr)₄; (j), MsCl, Et₃N; (k), Raney Nickel.

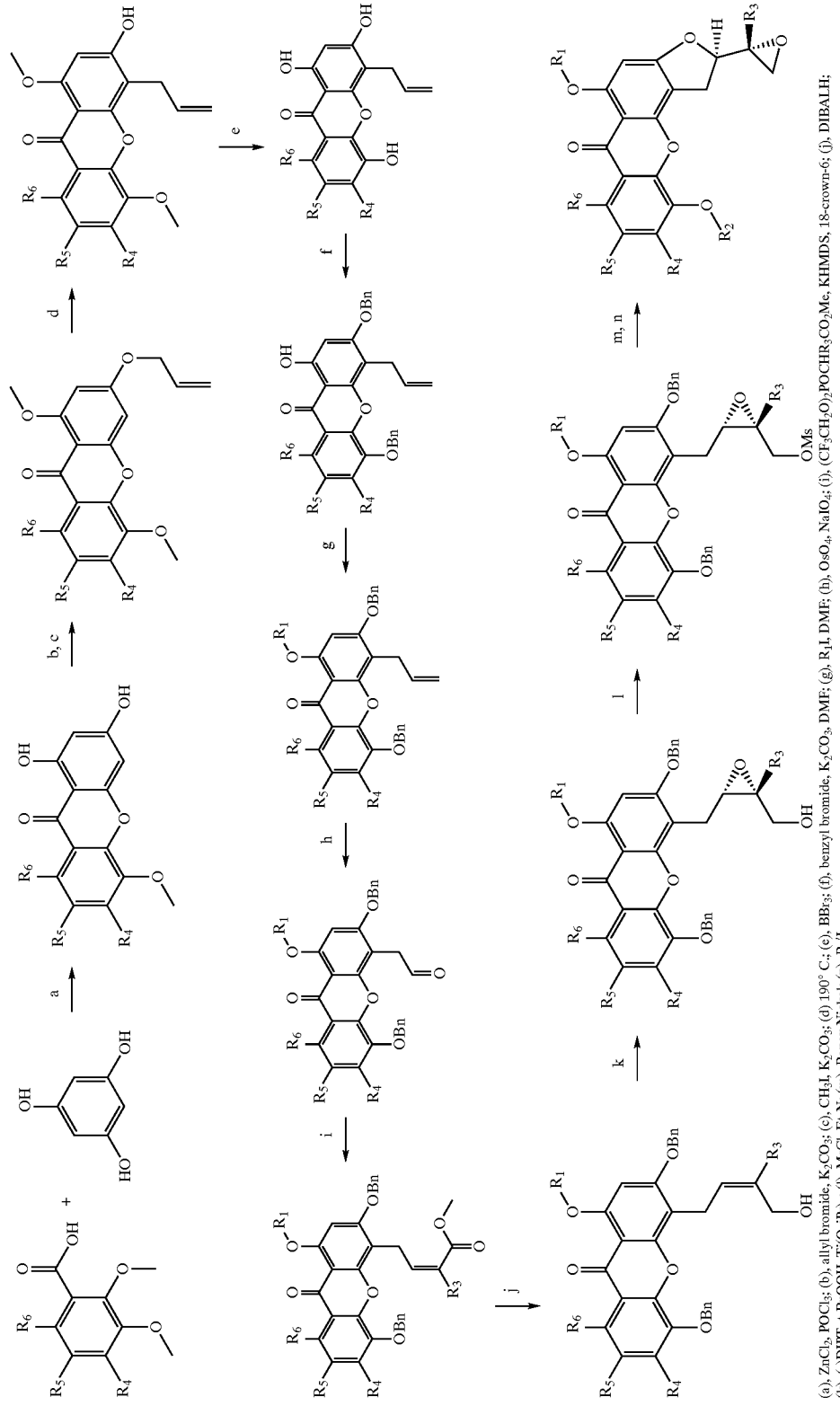

Reaction Scheme 5:
2'S,3'S Psorospermin and Closely Related Analogs (R2 = H)
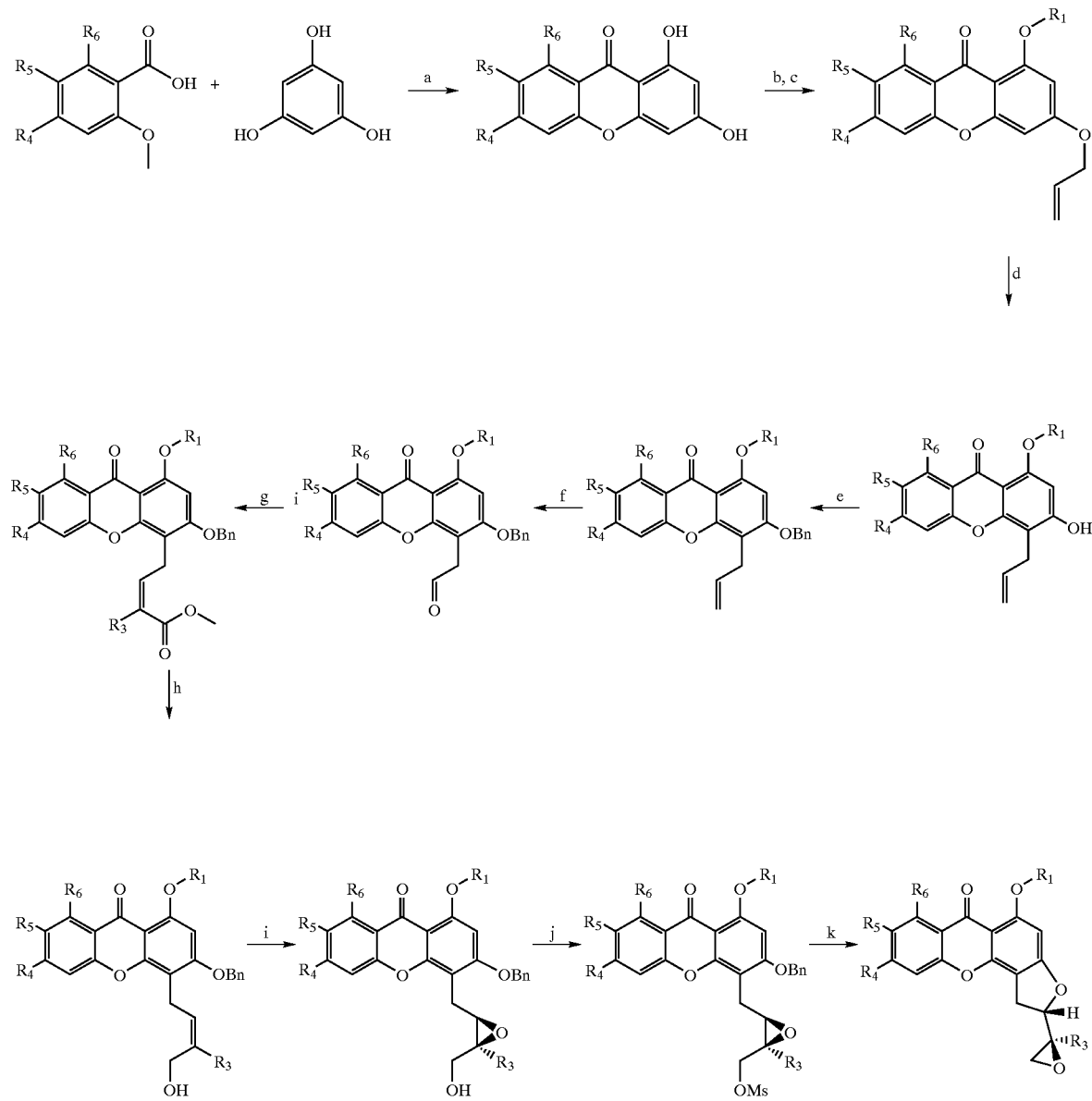
(a), ZnCl$_2$, POCl$_3$; (b), allyl bromide, K$_2$CO$_3$; (c), R$_1$I, K$_2$CO$_3$; (d) 190° C.; (e), benzyl bromide, K$_2$CO$_3$, DMF; (f), OsO$_4$, NaIO$_4$;
(g), (CF$_3$CH$_2$O)$_2$POCHR$_3$CO$_2$Me, KHMDS, 18-crown-6; (h), DIBALH; (i), (+)DIPT, t-BuOOH, Ti(O-iPr)$_4$; (j), MsCl, Et$_3$N; (k), Raney Nickel.

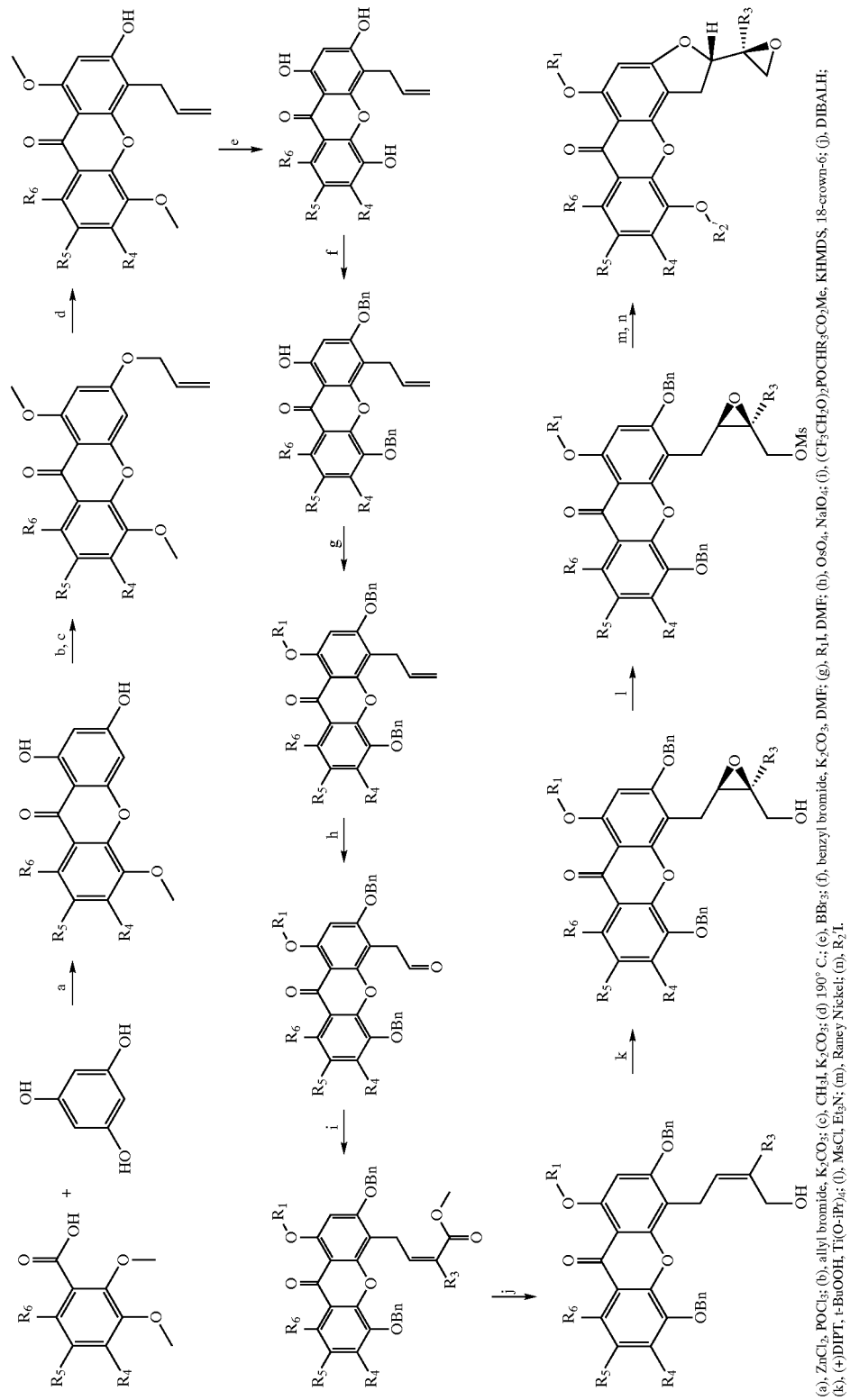

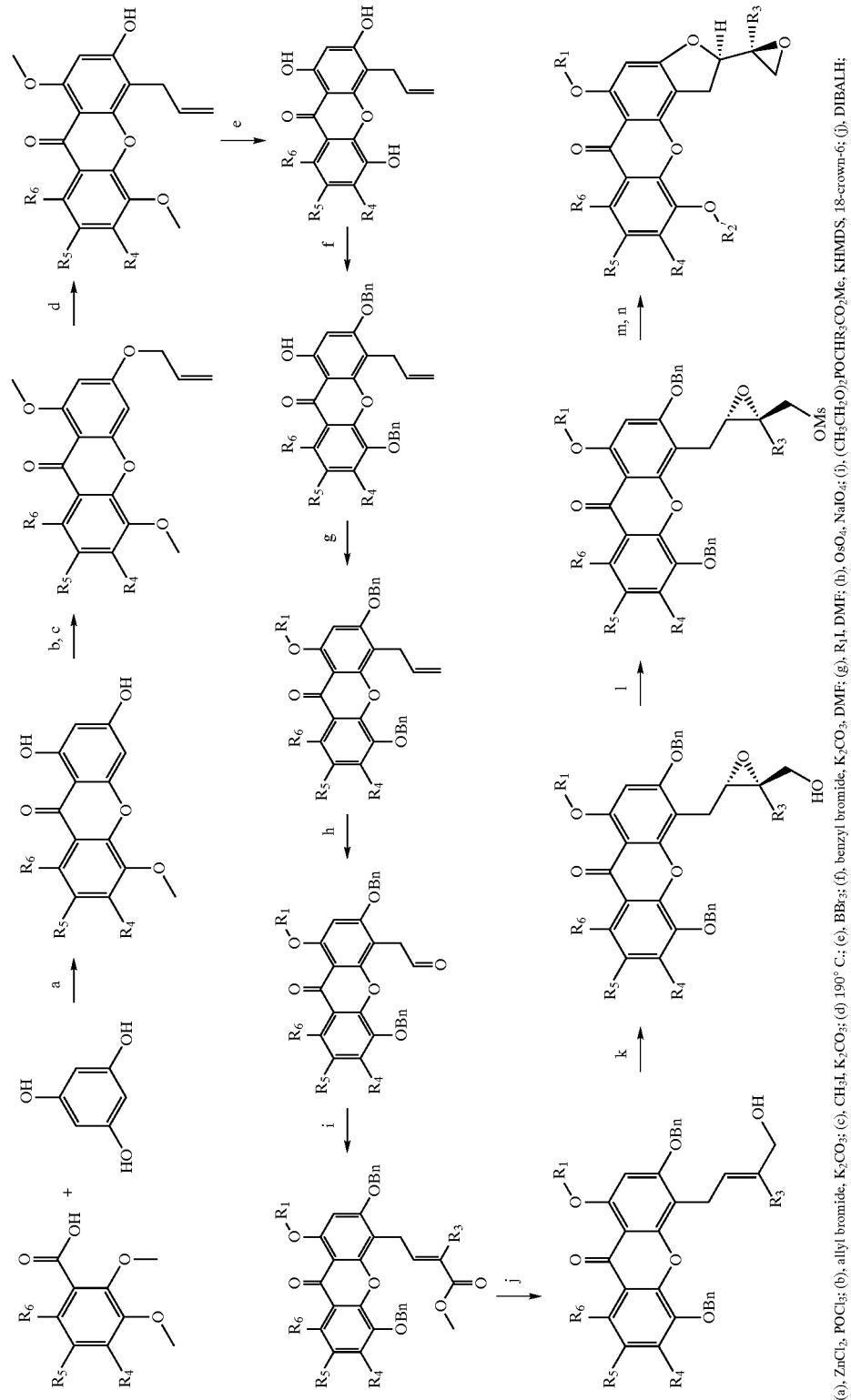

Reaction Scheme 8:
2′R,3′S Psorospermin and Closely Related Analogs (R2 = H)
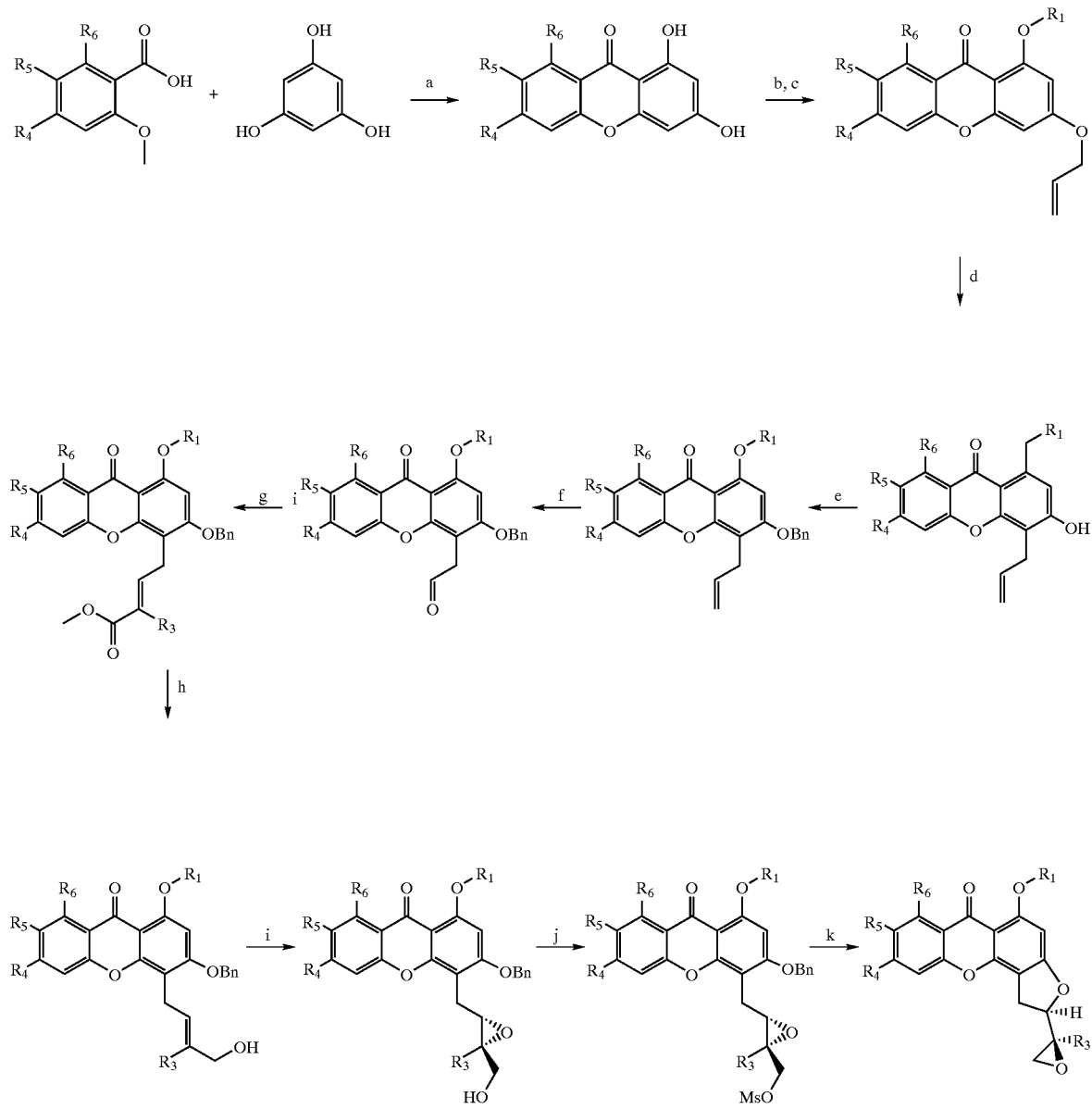
(a), ZnCl$_2$, POCl$_3$; (b), allyl bromide, K$_2$CO$_3$; (c), R$_1$I, K$_2$CO$_3$; (d) 190° C.; (e), benzyl bromide, K$_2$CO$_3$, DMF; (f), OsO$_4$, NaIO$_4$;
(g), (CH$_3$CH$_2$O)$_2$POCHR$_3$CO$_2$Me, KHMDS, 18-crown-6; (h), DIBALH; (i), (-)DIPT, t-BuOOH, Ti(O-iPr)$_4$; (j), MsCl, Et$_3$N; (k), Raney Nickel.

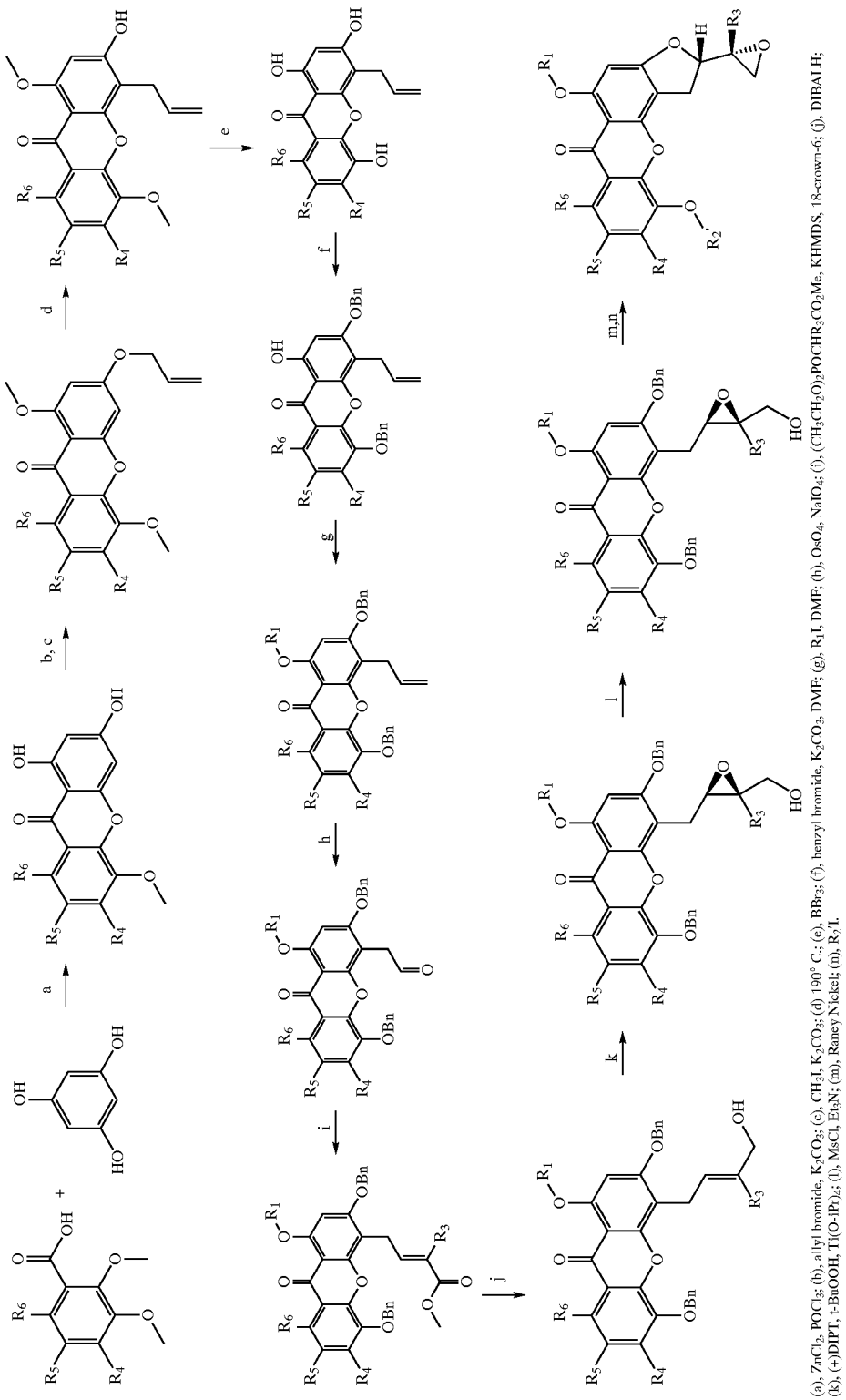

Reaction Scheme 10:
2'S,3'R Psorospermin and Closely Related Analogs (R2 = H)
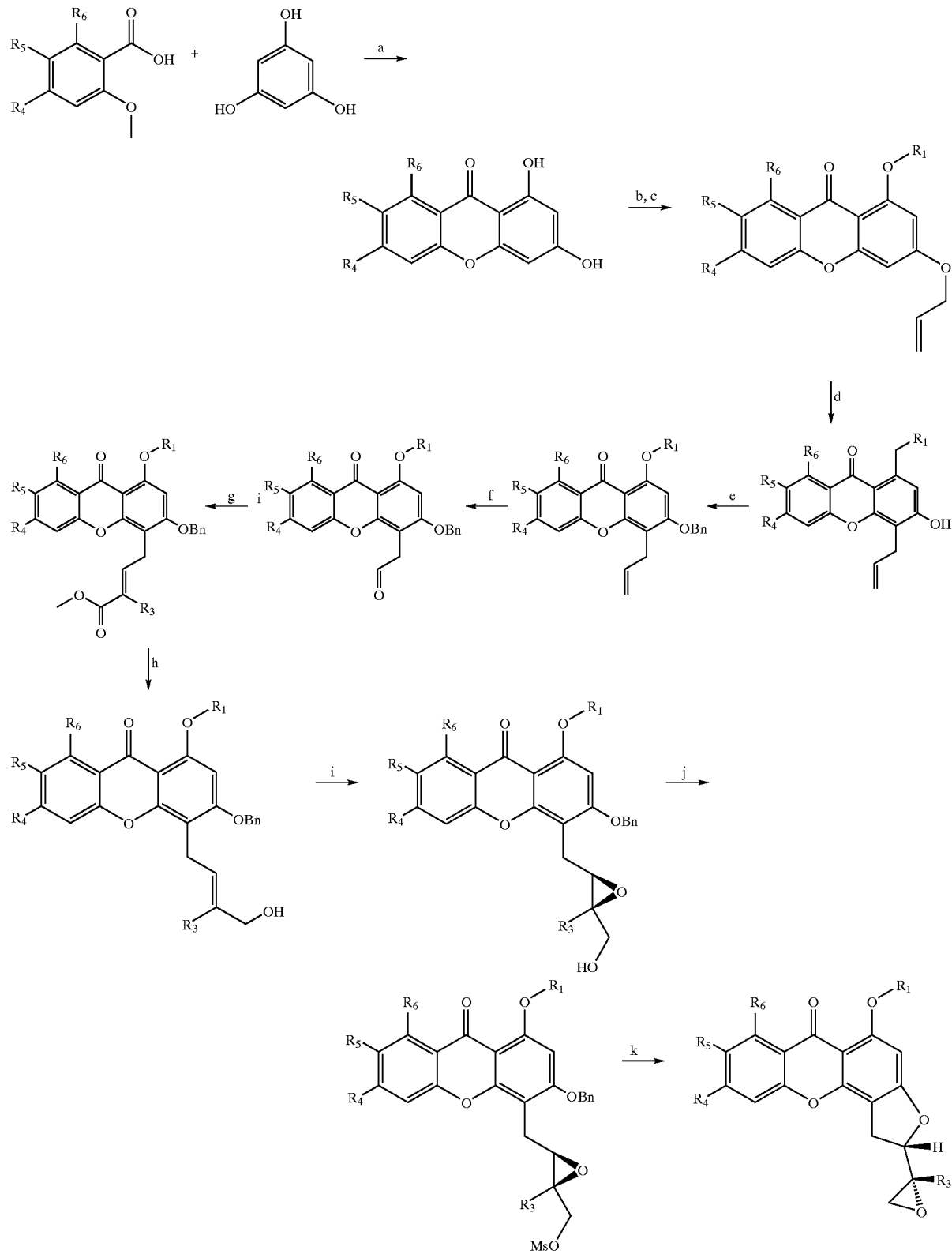
(a), $ZnCl_2$, $POCl_3$; (b), allyl bromide, $K_2CO_3$; (c), $R_1I$, $K_2CO_3$; (d) 190° C.; (e), benzyl bromide, $K_2CO_3$, DMF; (f), $OsO_4$, $NaIO_4$;
(g), $(CH_3CH_2O)_2POCHR_3CO_2Me$, KHMDS, 18-crown-6; (h), DIBALH; (i), (+)DIPT, t-BuOOH, Ti(O-iPr)$_4$; (j), MsCl, $Et_3N$; (k), Raney Nickel.

Administration and Use

The compounds of the invention are useful among other indications in treating conditions associated with proliferative disorders. Thus, the compounds described above or their pharmaceutically acceptable salts are used in the manufacture of a medicament for prophylactic or therapeutic treatment of mammals, including humans, in respect of conditions characterized by proliferative and/or differentiative disorders such as cancer and more specifically leukemia.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

It should be noted that the compounds of the invention can be administered as individual active ingredients, or as mixtures of several embodiments of this formula. In addition, the psorospermin compounds and analogs can be used as single therapeutic agents or in combination with other therapeutic agents.

As implied above, although the compounds of the invention may be used in humans, they are also available for veterinary use in treating animal subjects.

The following examples are intended to illustrate but not to limit the invention, and to further illustrate the use of the above Reaction Schemes.

EXAMPLES

Example 1

Synthesis of (2'R,3'R) Psorospermin

A. Synthesis of 5-Methoxy-1,3-dihydroxy-xanthone, 1

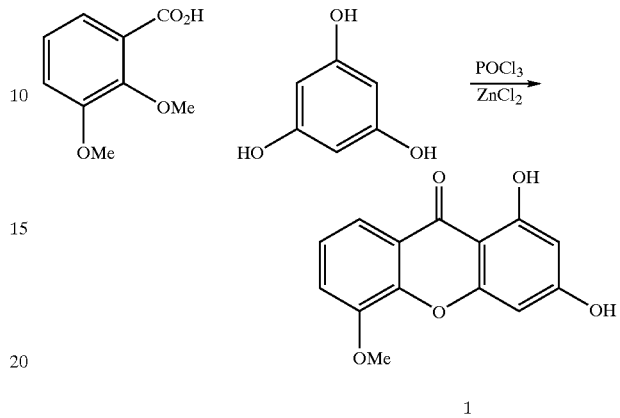

1

To a dry 2L roundbottom flask, fitted with a condenser and a mechanical stirrer, was added zinc chloride (200 g, 1.47 mol) followed by phosphorus oxychloride (720 mL, 7.71 mol) and the mixture was warmed to 50° C. for 30 minutes. 2,3-Dimethoxybenzoic acid (250 g, 1.37 mol) was added and the mixture was stirred for an additional hour. Phlorglucinol (200 g, 1.58 mol) was then added and the reaction mixture was allowed to stir until tlc analysis indicated complete disappearance of the dimethoxybenzoic acid (30–60 minutes). The reaction mixture was allowed to cool to room temperature and slowly poured into 10L ice water with constant mechanical stirring for 20 minutes. The aqueous layer was decanted from the red solid and replaced with 3L water and stirred for an additional 5 minutes. The resulting solid was collected by filtration and dissolved in 1N NaOH at 50° C. The aqueous solution was neutralized with 1N HCl and the red solid was collected by filtration and dried in vacuo to afford the xanthone 1 as a red solid (270 g, 76%).

B. Synthesis of 5-Methoxy-3-allyloxy-1-hydroxy-xanthone, 2

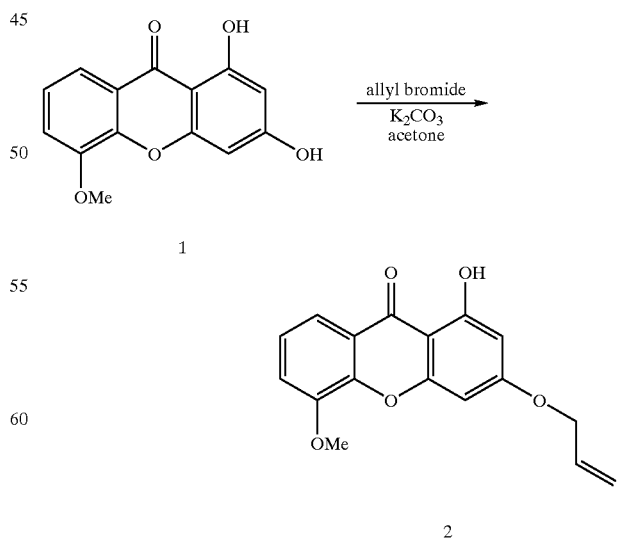

2

To a mixture of xanthone 1 (135, 0.52 mol) and potassium carbonate (145 g, 1.05 mol) in 1L dry acetone was added allyl bromide (71 g, 0.59 mol) and the mixture was refluxed under argon until tlc analysis indicated the reaction was complete (60 hours). The solvent was removed in vacuo and the resulting crude solid was taken up in 1.5L ethyl acetate and the remaining potassium carbonate was dissolved in dilute sulfuric acid. The organic layer was dried over magnesium sulfate, filtered and concentrated in vacuo. The crude solid was taken up in 1L acetone and filtered over a pad of silica gel (80×100 mm) and the solvent removed in vacuo to afford the xanthone 2 as a pale yellow solid (150 g).

C. Synthesis of 5-methoxy-3-allyloxy-1-methoxy-xanthone, 3

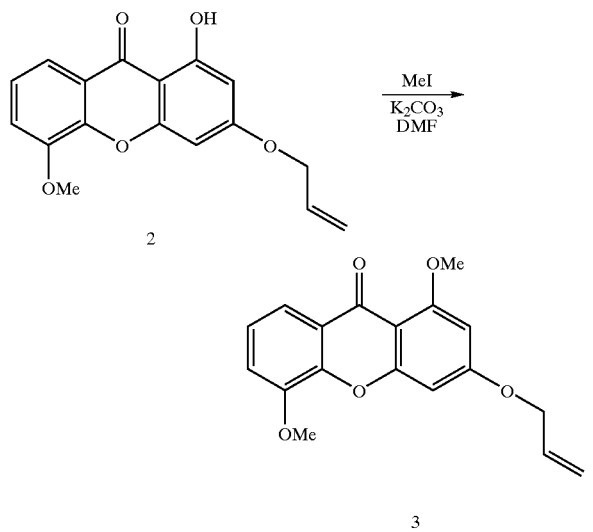

To a solution of xanthone 2 (150 g, 0.5 mol) in dry DMF (500 mL) was added potassium carbonate (100 g, 0.72 mol) and methyl iodide (180 g, 1.28 mol) and the mixture was heated with constant stirring under argon to 80° C. for 1 hour. The mixture was allowed to cool to room temperature and diluted with 2L ethyl acetate and the remaining potassium carbonate was dissolved in dilute sulfuric acid. The organic layer was dried over magnesium sulfate, filtered and concentrated in vacuo to afford the xanthone 3 (120 g, 0.38 mol, 77%) as a pale yellow solid.

D. Synthesis of 1,5-dimethoxy-4-allyl-xanthone, 4

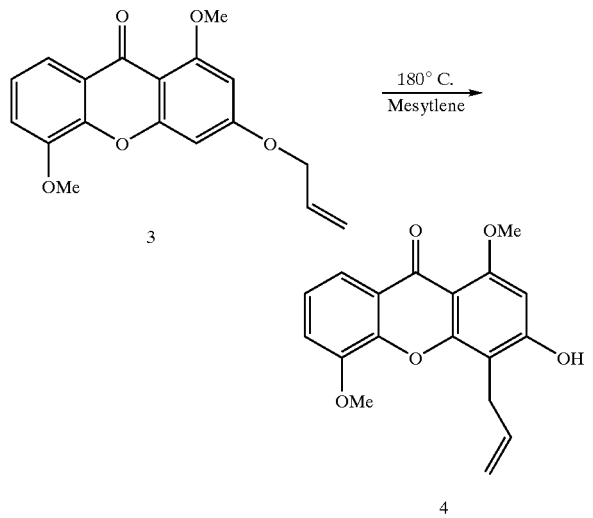

Xanthone 3 (120 g, 0.38 mol) was heated to reflux in mesytlene (300 mL) for 36 hours. Upon cooling the product was removed by filtration and washed with ether (300 mL) to afford xanthone 4 as a white solid (58 g, 186 mmol, 42%).

E. Synthesis of 1,3,5-trihydroxy-4-allyl-xanthone, 5

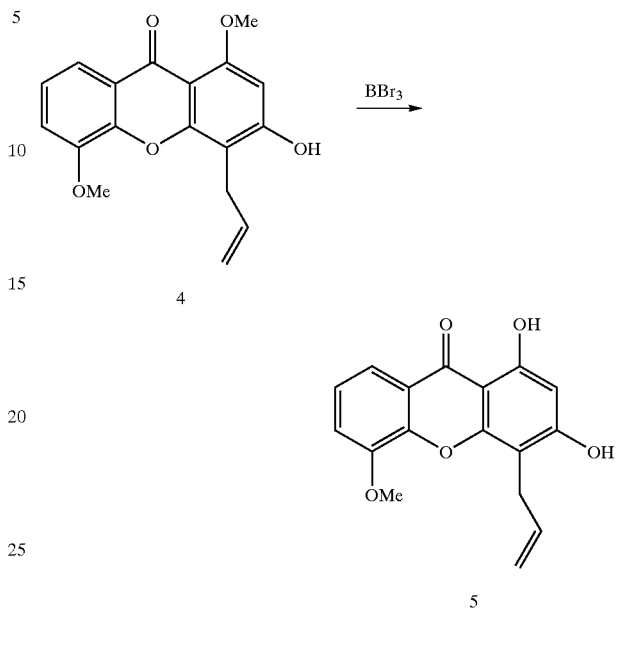

To a suspension of xanthone 4 (58 g, 186 mmol) in methylene chloride (200 mL) at −20° C. was added boron tribromide (650 mL, 650 mol) over 5 minutes. The reaction mixture was allowed to warm to room temperature and stirred for an additional 1.5 hours. The crude mixture was then poured over ice and the product was collected by filtration and dried in vacuo to afford the xanthone 5 as a white solid (48 g, 168 mmol, 91%).

F. Synthesis of 3,5-dibenzyloxy-1-hydroxy-4-allyl-xanthone, 6

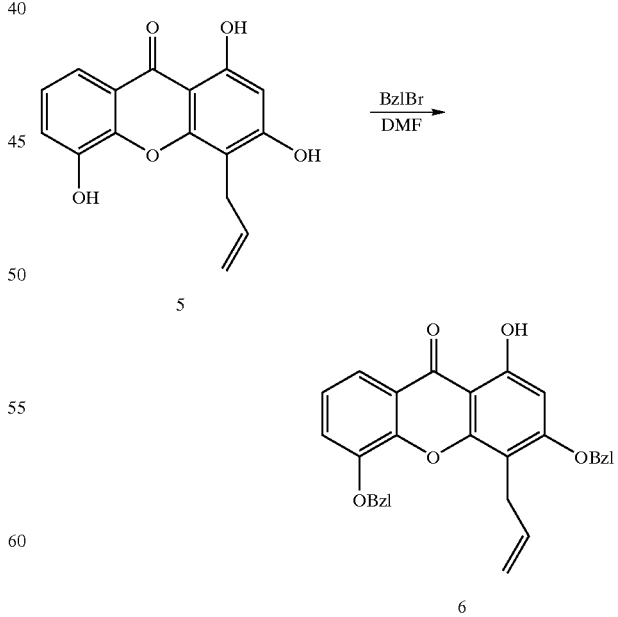

To a solution of xanthone 5 (48 g, 168 mmol) in dry DMF was added potassium carbonate (46 g, 336 mmol) and benzyl bromide (90 g, 526 mmol) and the mixture was heated to 110° C. for 8 hours. The reaction mixture was cooled to room temperature, diluted with ethyl acetate (1.4L) and the remaining potassium carbonate was destroyed with 2M Sulfuric acid. The organic layer was washed with brine (2×500 mL), dried over magnesium sulfate and concentrated in vacuo to afford the xanthone 6 as a solid (63 g, 135 mmol, 81%).

G. Synthesis of 3,5-dibenzyloxy-1-methoxy-4-allyl-xanthone, 7

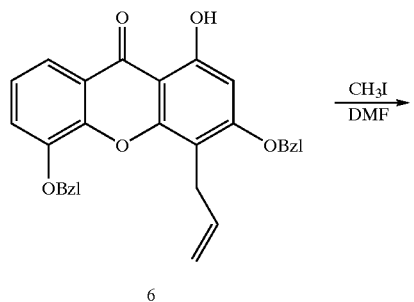

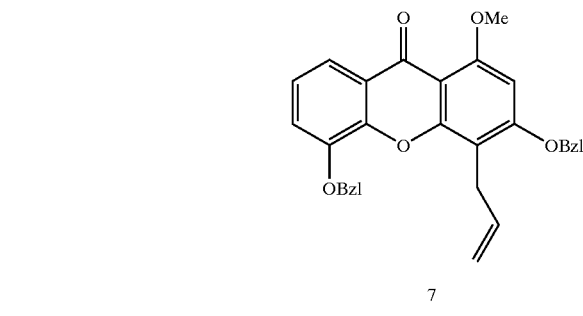

To a solution of xanthone 6 (63 g, 135 mmol) in dry DMF (300 mL) was added sodium hydride (9 g 60% in oil, 225 mmol) portionwise at room temperature. Methyl Iodide (180 g, 1.28 mol) was added and the mixture was heated to 50° C. for 90 minutes. The reaction was then chilled with an ice bath and methanol was added dropwise (20 mL) until the remaining sodium hydride was consumed. The reaction mixture was diluted with ethyl acetate (1.2L) and washed with brine (3×500 mL), dried over magnesium sulfate, filtered over a pad of silica gel (60×100 mm) and the solvent was removed in vacuo to afford the xanthone 7 as a solid (55 g, 115 mmol, 85%).

H. Synthesis of 3,5-dibenzyloxy-1-methoxy-xanthone-4-aldehyde, 8

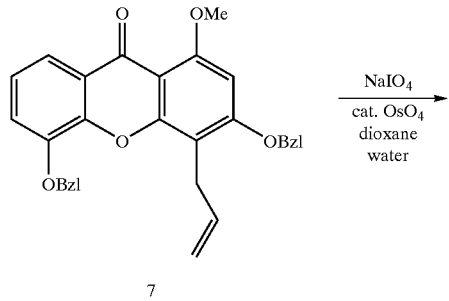

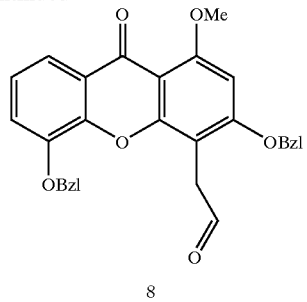

To a solution of xanthone 7 (54 g, 113 mmol) dissolved in dioxane (600 mL) was added water (200 mL) and osmium tetroxide (4 mL 4% solution in water) and the mixture was allowed to stir for 5 minutes. Sodium periodate (100 g, 469 mmol) was then added and the reaction mixure was heated to 35° C. for 3 hours. The reaction mixture was allowed to cool to room temperature, diluted with ethyl acetate (1L), washed with water and dried over magnesium sulfate. The solvent was removed in vacuo to afford a brown oil (56 g) which was crystallized from THF to afford the xanthone 8 as a white solid (15 g). The remaining filtrate was chromatographed on silica gel (1:1 ethyl acetate/hexanes) to afford more of the xanthone 8 (9 grams, 24 grams total, 50 mmol, 44%).

I. Synthesis of 1,3,5-trialkoxy-4-eneoate-xanthone, 9

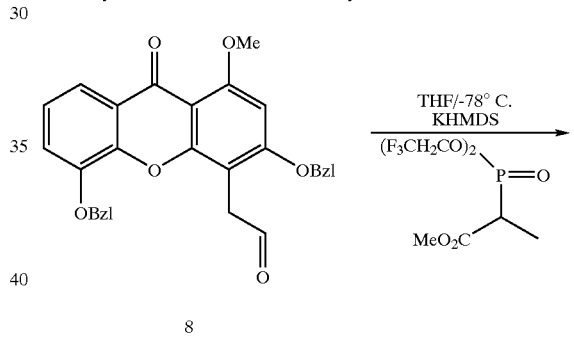

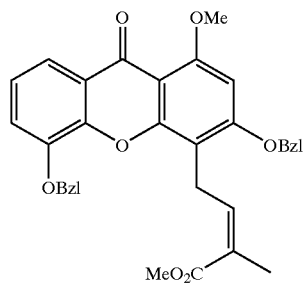

To a solution of the phosphonate (Still, W. C. et.al., Tetrahedron Letters, 1983, 41, 4405. ) (8 g, 24 mmol) and 18-crown-6 (15 g, 57 mmol) in dry THF (300 mL) at −78° added KHMDS (50 mL, 0.5 M in toluene, 25 mmol) and the reaction mixture was allowed to stir for 30 minutes under argon. The aldehyde 8 was then added as a dry powder and the reaction mixture was stirred for 6 hours at −78° C. then allowed to slowly warm to room temperature overnight. The mixture was then diluted with ethyl acetate (1.2L), washed with water (4×500 mL), dried over magnesium sulfate and the solvent was removed in vacuo to afford the xanthone 9 as a mixture of E and Z isomers (10 g, E:Z/1:10). The Z isomer was purified by recrystallization from ethyl acetate to afford pure xanthone Z-ester 9.

J. Synthesis of Allylic Alcohol, 10

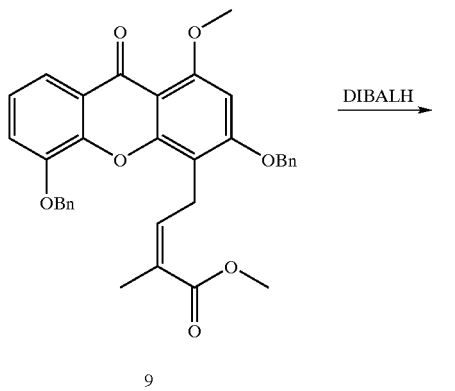

9

To a solution of xanthone Z-ester 9 (5.0 g, 9.1 mmol) in methylene chloride (200 mL) at −78° C. was added DiBALH (18.2 mL, 1.0M in $CH_2Cl_2$) dropwise and the reaction was allowed to stir for 30 minutes. The reaction was quenched with 1N HCl and allowed to warm to room temperature. The mixture was extracted with methylene chloride, dried over sodium sulfate and the solvent was removed in vacuo. The resulting material was purified on silica gel (50% EtOAC/Hexanes) to afford the allylic alcohol 10 as a white solid (3.86 g, 7.39 mmol).

K. Synthesis of Epoxy Alcohol, 11

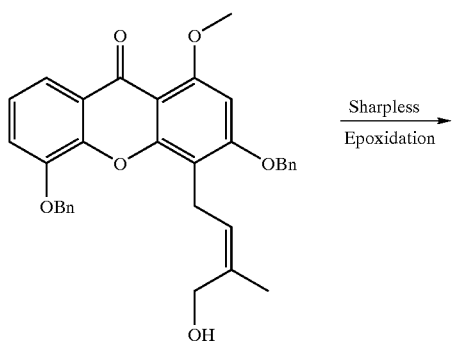

10

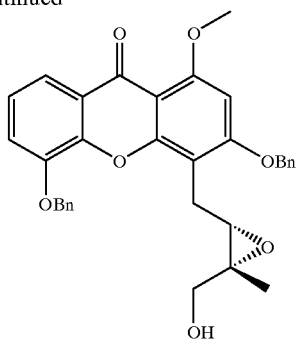

11

To freshly dried 3 Å molecular sieves (2.0 g) in methylene chloride (60 mL) was added (−) diisopropyl tartrate (2.08 g, 8.87 mmol) and the mixture was chilled to 0° C. with an ice bath. Titanium isopropoxide (2.6 mL, 8.87 mmol) was then added and the mixture was allowed to stir for 15 minutes. The reaction was then cooled to −78° C. and the allylic alcohol 10 (3.86 g, 7.39 mmol) dissolved in methylene chloride (10 mL) was added followed by tert-butyl hydroperoxide (7.4 mL, 5M in decane, 44 mmol). The reaction was then allowed to stir at −25° C. overnight. The mixture was then filtered to remove the solids and then stirred with a sodium hydrogen sulfite solution for 1 hour. The resulting mixture was then extracted with methylene chloride (3×100 mL), dried over sodium sulfate and concentrated in vacuo. The resulting oil was chromatographed on silica gel (50% ethyl acetate/hexanes) to remove the residual hydroperoxide and to afford the allylic alcohol 11 as a white solid (3.1 g, 5.76 mmol, 78%)

L. Synthesis of Mesylate, 12

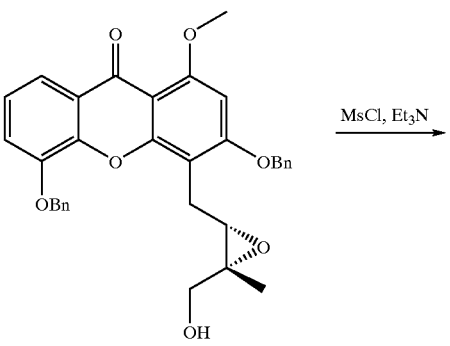

11

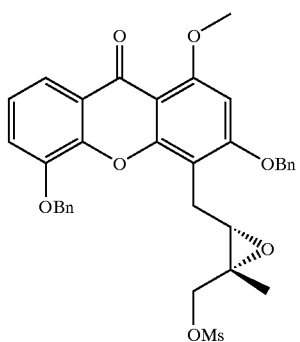

12

To a solution of the epoxy alcohol 11 (3.1 g, 5.76 mmol), dissolved in methylene chloride (60 mL) was added methanesulfonyl chloride (0.5 mL, 6.34 mmol) at 0° C. Triethylamine (0.96 mL, 6.9 mmol) was then added dropwise and the reaction mixture was allowed to stir for 30 minutes. The reaction was then quenched with 1N HCl, and the organic layer was washed with brine, dried over sodium sulfate, and filtered over a pad of silica gel (10×20 mm). The resulting liquid was dried in vacuo and recrystallized (EtOAc/EtOH) to afford the mesylate 12 as a white solid (3.4 g, 5.5 mmol, 95%).

M.(1) Synthesis of (2'R,3'R) Psorospermin, 13

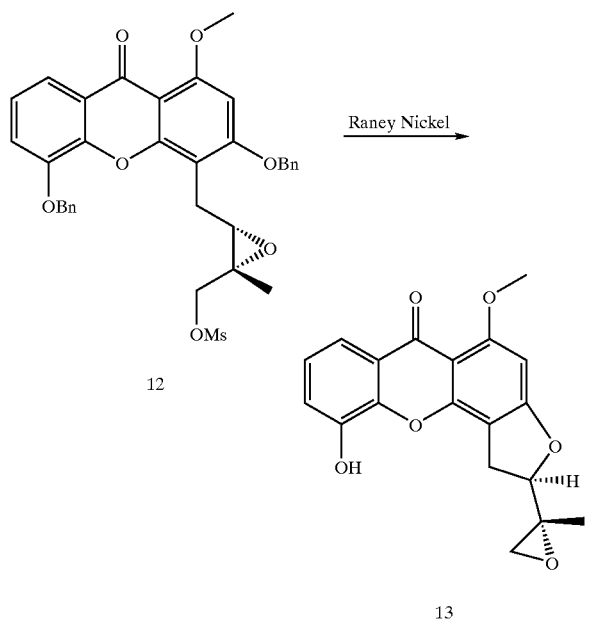

To a solution of the mesylate 12 (1.0 g, 1.6 mmol) dissolved in a 50/50 mixture of dry ethyl acetate/absolute ethanol (60 mL each) and potassium carbonate (300 mg, 2.17 mmol) was added Raney Nickel (0.5 mL slurry) and the reaction was heated to 60° C. More Raney Nickel was added while monitoring the reaction via tlc analysis. Upon completion of the reaction the catalyst was filtered (pyrophoric) and the solvent was removed in vacuo. The resulting material was chromatographed on silica gel (5% MeOH/CH$_2$Cl$_2$) to afford Psorospermin (380 mg, 1.11 mmol, 70%) as a white solid).

M.(2) Alternate Synthesis of Psorospermin, 13

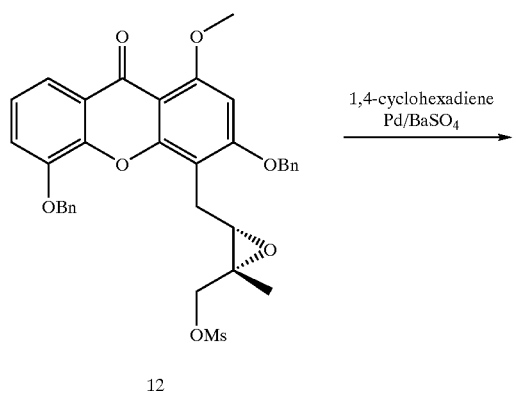

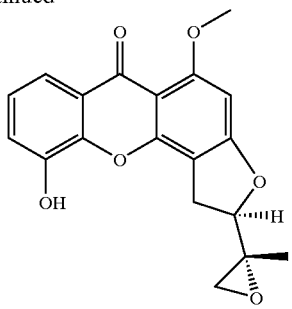

13

To a solution of the epoxy xanthone 12 (470 mg, 0.76 mmol) dissolved in dry absolute ethanol and ethyl acetate (60 ml each) was added 1,4-cyclohexadiene (2.0 mL) and Pd/BaSO$_4$ (50 mg) and the mixture was heated at 80° C. for 2 hours. The catalyst was then filtered and potassium carbonate was added (200 mg, 1.45 mmol) followed by dry methanol (50 mL) and the reaction mixture was stirred for an additional 30 minutes. The solvent was removed in vacuo and the residue was chormatographed on silica gel (5% MeOH/CH$_2$Cl$_2$) to afford Psorospermin 13 as a white solid (172 mg, 0.51 mmol, 67%).

Example 2

Synthesis of (2'R,3'R) 5-Methoxy Psorospermin, 14

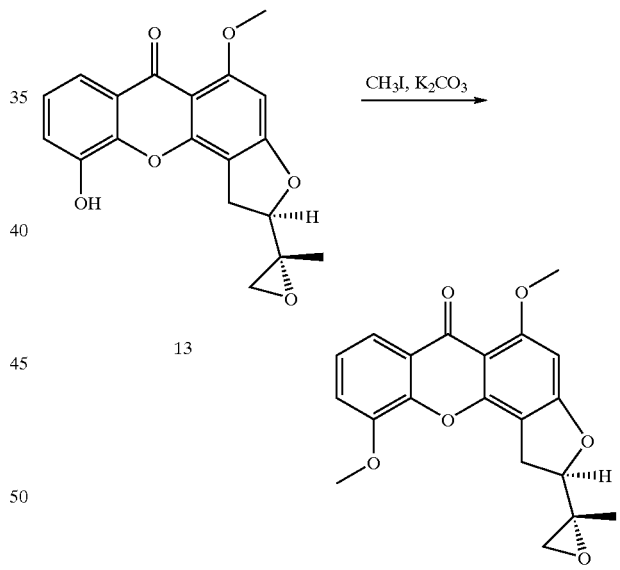

(2'R,3'R) Psorospermin (10 mg) was dissolved in acetone (10 ml) and refluxed with methyl iodide (0.05 ml) and potassium carbonate for 30 mins. The resulting mixture was evaporated to give a residue of the methyl ether.

Example 3

MTS cytotoxicity data was collected for a comparison of (R,R)-psorospermin with (R,R)-5-methoxy-psorospermin, (R,S)-5-methoxy-psorospermin, (S,R)-5-methoxy-psorospermin and (S,S)-5-methoxy-psorospermin in cell viability assays with various tumor cell lines, the results of which are shown in FIG. 1.

Example 4

Studies have shown that the (2R',3R') 5-methoxy psorospermin and analogs thereof are more active than their (2R', 3S') or (2S', 3S') counterparts.

(R,R)-5-Methoxypsorospermin surprisingly showed comparable antitumor activity to that of the natural product psorospermin in a variety of cell lines including those of solid tumors and lymphomas. However, when the pharmacokinetics of the natural product was compared to the 5-methoxy analogue by intravenous injections of a 5 mg dose in rats, the 5-methoxy compound was found to give prolonged measurable quantities of the parent with a good half life giving an excellent overall profile where as the natural product could be barely detected at any time point. Blood plasma levels of psorospermin over 24 h after a 5 mg/Kg injection i.v. in Sprague Dawley rats were measured. Little parent compound can be detected within the first 24 h after dosing as shown in FIG. 2. Blood plasma levels of 5-methoxy-psorospermin over 24 h after a 5 mg/Kg injection i.v. in Sprague Dawley rats were measured. The compound exhibits in rodents a therapeutic dose that exceeds two hours as shown in FIG. 3.

All references mentioned herein are incorporated herein by reference in their entirety.

What is claimed is:

1. A process for preparing a substantially optically pure psorospermin or analog of the formula:

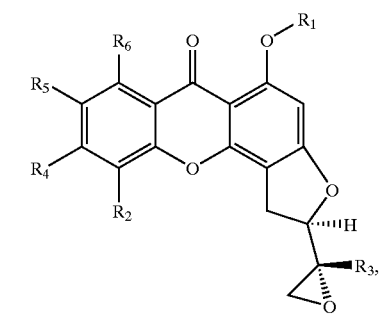
(1)

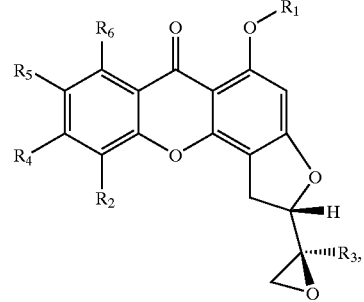

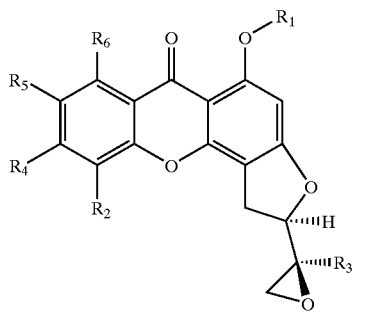
(2) or

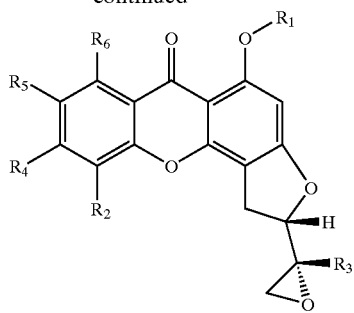

wherein each of $R_1$ and $R_3$ is H or alkyl;

wherein $R_2$ is H, OH, substituted or unsubstituted alkyl, $OR_2'$, wherein the substituted alkyl is 1–6C alkyl substituted with —$COOR_7$, —≡N, or heteroalkyl, wherein $R_7$ is H or alkyl, and wherein $R_2'$ is alkyl or a protecting group;

wherein each of $R_4$, $R_5$, and $R_6$ is H, alkyl, or 2–10C alkoxy; wherein two adjacent residues of $R_2$, $R_4$, $R_5$, and $R_6$ can form a fused cyclic, aromatic, heteroaromatic or heterocyclic ring having 5–7 members, the process comprising:

deprotecting a compound of the formula:

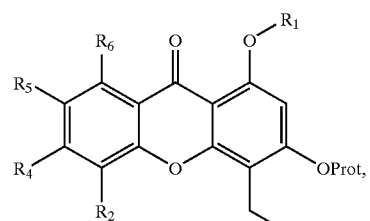

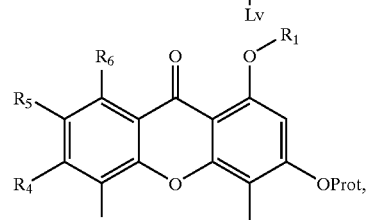

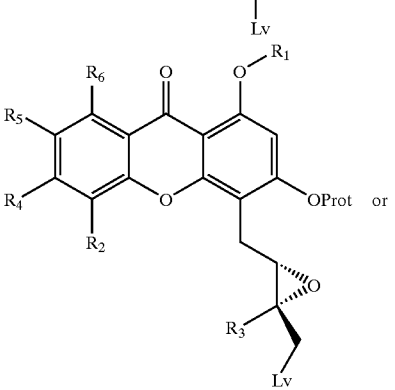

-continued

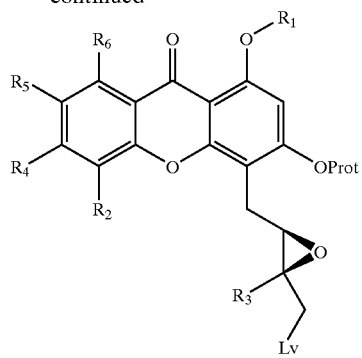

wherein $R_1$ and $R_3-R_6$ are defined above, $R_2$ is H, alkyl, O-alkyl, or an O-protecting group, Prot is a protecting group, and Lv is a leaving group.

2. The process of claim 1, wherein deprotecting conditions in the deprotection step comprise Pd/BaSO$_4$ and 1,4-cyclohexadiene, or Raney Nickel.

3. The process of claim 1, wherein $R_2$ is OH after the deprotecting step
wherein the process further comprises alkylating

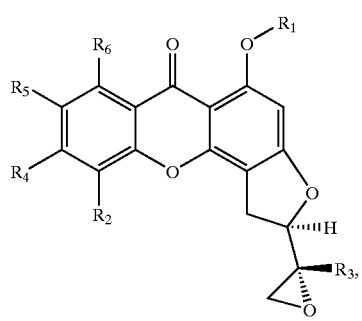

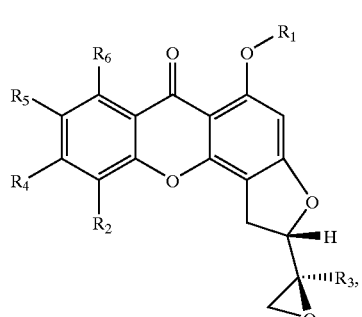

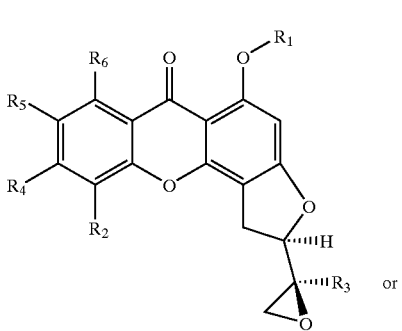

or

-continued

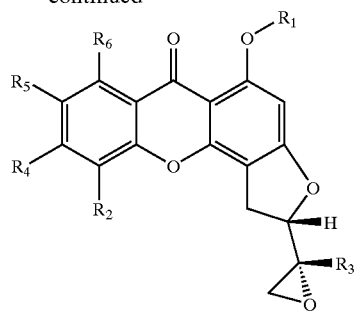

wherein $R_2$ is $OR_2'$ where $R_2'$ is alkyl after the alkylating step.

4. The process of claim 1 further comprising before the hydrogenating step,
chirally epoxidizing

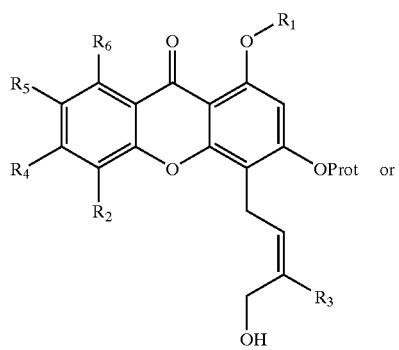

or

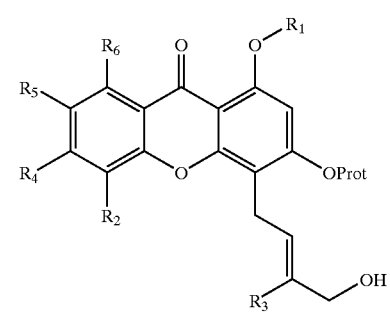

wherein $R_1$ and $R_3-R_6$ are defined as above and $R_2$ is H, alkyl or a protected hydroxyl group to form

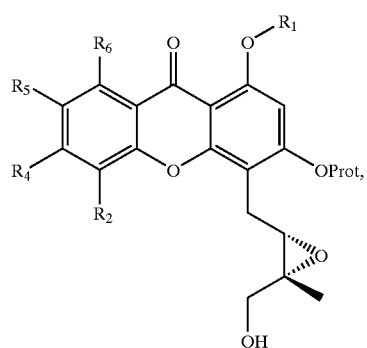

-continued

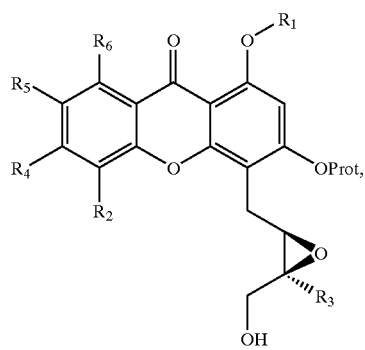

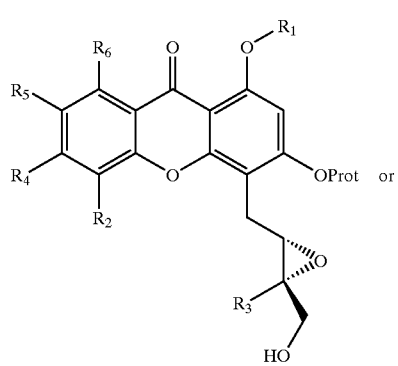

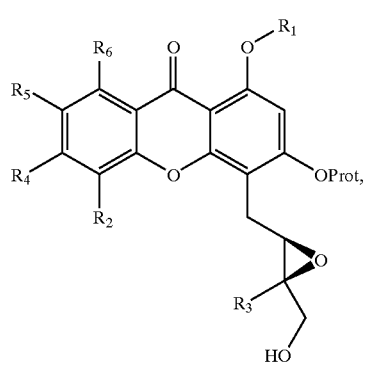

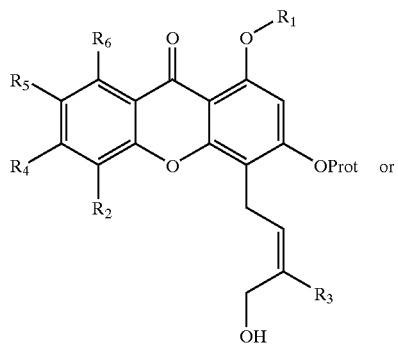

modifying the hydroxyl at the 4' position to form a leaving group.

5. The process of claim 4 wherein either of

-continued

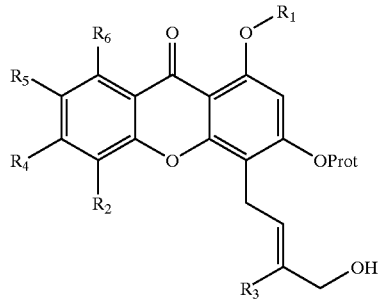

is epoxidized with of either (−) DIPT or (+) DIPT and the leaving group is provided by mesylation of the hydroxyl group.

6. The process of claim 4 further comprising before the chiral epoxidizing step, forming an unsaturated ester under either cis- or trans-directing reaction conditions

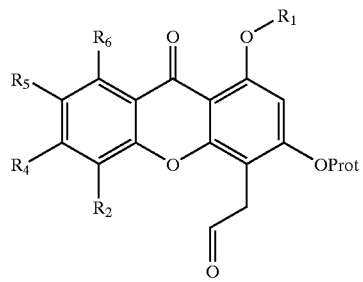

wherein $R_1$ and $R_4$–$R_6$ are defined above, $R_2$ is H, alkyl, O-alkyl, or an O-protecting group, and Prot is a protecting group to form a cis or trans ester of the formula

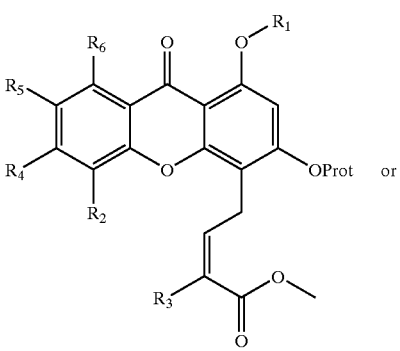

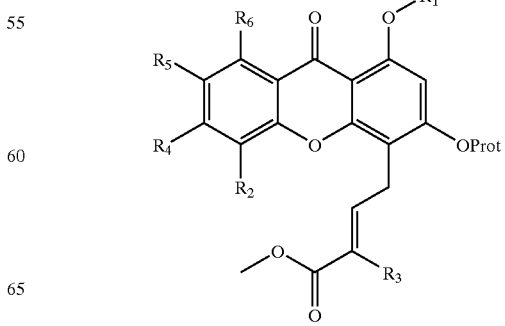

subsequently reducing the ester to an allylic alcohol of the formula

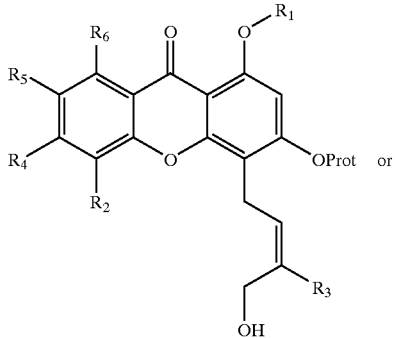

wherein $R_1$ and $R_3$–$R_6$ are defined above, $R_2$ is H, alkyl, O-alkyl, or an O-protecting group, and Prot is a protecting group.

7. The process of claim 6, wherein the cis ester is separated from the trans ester.

8. The process of claim 7, wherein the cis ester is separated by recrystalization from ethylacetate.

9. The process of claim 6 wherein the cis-directing reaction conditions are $(CF_3CH_2O)_2POCH(R_3)CO_2Me$ or $(PhO)_2POCH(R_3)CO_2R$, where R is an alkyl group and Ph can be substituted, in KHMDS/18-crown-6 and the trans-directing reaction conditions $(CH_3CH_2O)_2POCH(R_3)CO_2R$ wherein R is alkyl; and wherein the ester is reduced with DIBAL-H.

10. The process of claim 6 further comprising before the esterifying step, selectively protecting the hydroxyl group at the 3 position and a hydroxyl group at the 5 position, if $R_2$ is OH as in the following compound:

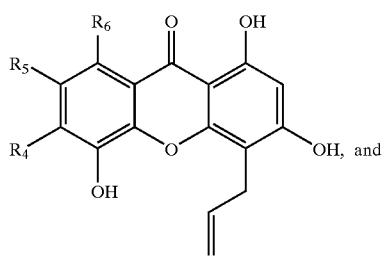

wherein $R_1$ and $R_4$–$R_6$ are defined above, to form

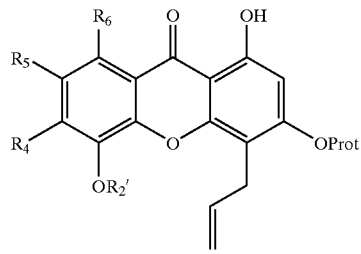

wherein $R_2$ is $OR_2'$ and $R_2'$ is a protecting group, OProt is a protected hydrokyl group and $R_1$ and $R_4$–$R_6$ are defined above, alkylating the hydroxyl group at the 1 position, and forming an aldehyde at the 3' position to form

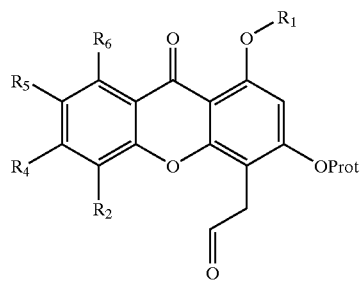

wherein $R_2$ is $OR_2'$ and $R_2'$ is a protecting group.

11. The process of claim 10, wherein the protecting group on the hydroxyl group at the 3 and 5 positions is a benzyl group.

12. The process of claim 10, further comprising before the protecting step, dealkylating

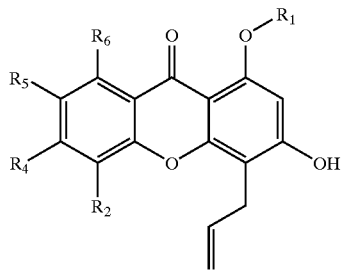

wherein $R_1$ is alkyl and $R_2$ is $OR_2'$ and $R_2'$ is alkyl, and wherein $R_4$–$R_6$ are as defined above, to form

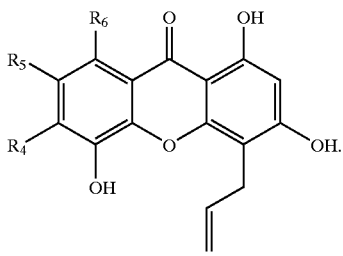

13. The process of claim 12, wherein $R_1$ and $R_2$ are each methyl before the dealkylating step and $BBr_3$ is used as a demethylation agent in the dealkylating step.

14. The process of claim 12 further comprising before the dealkylating step rearranging

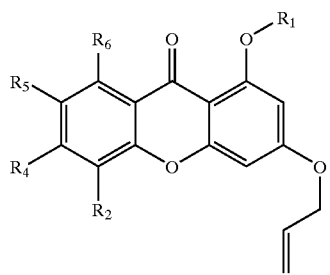

wherein $R_1$ is alkyl and $R_2$ is $OR_2'$ and $R_2'$ is alkyl to form

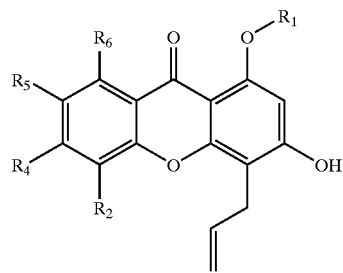

wherein $R_1$ is alkyl and $R_2$ is $OR_2'$ and $R_2'$ is alkyl under Claisen conditions such that cyclization does not result.

15. The process of claim 14 wherein the Claisen conditions comprise heating about 190° C.

16. The process of claim 1, wherein R,R psorospermin is produced.

17. The process of claim 1, wherein R,S psorospermin is produced.

18. The process of claim 1, wherein S,R psorospermin is produced.

19. The process of claim 1, wherein S,S psorospermin is produced.

20. The process of claim 1, wherein R,R 5-methoxypsorospermin is produced.

21. The process of claim 1, wherein R,S 5-methoxypsorospermin is produced.

22. The process of claim 1, wherein S,R 5-methoxypsorospermin is produced.

23. The process of claim 1, wherein S,S 5-methoxypsorospermin is produced.

24. A pharmaceutical composition comprising the substantially optically pure compound produced by the process in claim 1, and a pharmaceutically acceptable carrier, wherein $R_2$ is H, substituted or unsubstituted alkyl, wherein the substituted alkyl is 1–6C alkyl subsutituted with —$COOR_7$, —≡N, or heteroalkyl, wherein $R_7$ is H or alkyl.

* * * * *